United States Patent
Sanborn

(10) Patent No.: US 11,559,643 B2
(45) Date of Patent: Jan. 24, 2023

(54) SYSTEMS AND METHODS FOR VENTILATION OF PATIENTS

(71) Applicant: Covidien LP, Mansfield, MA (US)

(72) Inventor: Warren G. Sanborn, Escondido, CA (US)

(73) Assignee: Covidien LP, Mansfield, MA (US)

( * ) Notice: Subject to any disclaimer, the term of this patent is extended or adjusted under 35 U.S.C. 154(b) by 1122 days.

(21) Appl. No.: 16/174,945

(22) Filed: Oct. 30, 2018

(65) Prior Publication Data

US 2019/0143059 A1   May 16, 2019

Related U.S. Application Data

(60) Provisional application No. 62/725,490, filed on Aug. 31, 2018, provisional application No. 62/586,077, filed on Nov. 14, 2017.

(51) Int. Cl.
*A61M 16/00* (2006.01)
*G06F 3/04847* (2022.01)

(52) U.S. Cl.
CPC ...... *A61M 16/024* (2017.08); *A61M 16/0003* (2014.02); *A61M 16/0051* (2013.01); *G06F 3/04847* (2013.01); *A61M 2016/0018* (2013.01); *A61M 2016/0027* (2013.01); *A61M 2016/0033* (2013.01); *A61M 2205/18* (2013.01); *A61M 2205/3331* (2013.01); *A61M 2205/3334* (2013.01); *A61M 2205/502* (2013.01); *A61M 2230/42* (2013.01); *A61M 2230/46* (2013.01); *A61M 2230/60* (2013.01)

(58) Field of Classification Search
CPC .............................................. A61M 16/0051
See application file for complete search history.

(56) References Cited

U.S. PATENT DOCUMENTS

| | | | |
|---|---|---|---|
| 3,669,108 A | 6/1972 | Sundblom et al. |
| 4,127,123 A | 11/1978 | Bird |
| 4,448,192 A | 5/1984 | Stawitcke et al. |
| 4,527,557 A | 7/1985 | DeVries et al. |

(Continued)

FOREIGN PATENT DOCUMENTS

| | | |
|---|---|---|
| EP | 982043 | 3/2000 |
| EP | 1491227 | 12/2004 |

(Continued)

OTHER PUBLICATIONS

Canadian Office Action in Application 3046571, dated Jul. 24, 2019, 4 pages.

(Continued)

*Primary Examiner* — LaToya M Louis

(57) ABSTRACT

A mechanical ventilator is provided that includes a dashboard display identifying a patient's current ventilatory status within a global or universal ventilatory mechanics map. This dashboard display is dynamically updated with the patient's condition, and shows trends in the patient's ventilation over time. The map identifies suggested safe and unsafe regions of ventilation for the patient, and the ventilator can display informational texts, trigger auditory and/or visual alarms, and transmit alarm communications in response to determining that the patient is approaching or has entered an unsafe region.

20 Claims, 7 Drawing Sheets

(56) References Cited

U.S. PATENT DOCUMENTS

| | | |
|---|---|---|
| 4,637,385 A | 1/1987 | Rusz |
| 4,655,213 A | 4/1987 | Rapoport et al. |
| 4,752,089 A | 6/1988 | Carter |
| 4,773,411 A | 9/1988 | Downs |
| 4,805,612 A | 2/1989 | Jensen |
| 4,805,613 A | 2/1989 | Bird |
| 4,821,709 A | 4/1989 | Jensen |
| 4,921,642 A | 5/1990 | LaTorraca |
| 4,954,799 A | 9/1990 | Kumar |
| 4,986,268 A | 1/1991 | Tehrani |
| 5,044,362 A | 9/1991 | Younes |
| 5,057,822 A | 10/1991 | Hoffman |
| 5,072,737 A | 12/1991 | Goulding |
| 5,107,830 A | 4/1992 | Younes |
| 5,148,802 A | 9/1992 | Sanders et al. |
| 5,150,291 A | 9/1992 | Cummings et al. |
| 5,161,525 A | 11/1992 | Kimm et al. |
| 5,165,398 A | 11/1992 | Bird |
| 5,237,987 A | 8/1993 | Anderson et al. |
| 5,239,995 A | 8/1993 | Estes et al. |
| 5,271,389 A | 12/1993 | Isaza et al. |
| 5,279,549 A | 1/1994 | Ranford |
| 5,299,568 A | 4/1994 | Forare et al. |
| 5,301,921 A | 4/1994 | Kumar |
| 5,303,698 A | 4/1994 | Tobia et al. |
| 5,307,795 A | 5/1994 | Whitwam et al. |
| 5,313,937 A | 5/1994 | Zdrojkowski |
| 5,319,540 A | 6/1994 | Isaza et al. |
| 5,325,861 A | 7/1994 | Goulding |
| 5,333,606 A | 8/1994 | Schneider et al. |
| 5,339,807 A | 8/1994 | Carter |
| 5,343,857 A | 9/1994 | Schneider et al. |
| 5,351,522 A | 10/1994 | Lura |
| 5,353,788 A | 10/1994 | Miles |
| 5,357,946 A | 10/1994 | Kee et al. |
| 5,368,019 A | 11/1994 | LaTorraca |
| 5,383,449 A | 1/1995 | Forare et al. |
| 5,385,142 A | 1/1995 | Brady et al. |
| 5,390,666 A | 2/1995 | Kimm et al. |
| 5,398,676 A | 3/1995 | Press et al. |
| 5,401,135 A | 3/1995 | Stoen et al. |
| 5,402,796 A | 4/1995 | Packer et al. |
| 5,407,174 A | 4/1995 | Kumar |
| 5,413,110 A | 5/1995 | Cummings et al. |
| 5,433,193 A | 7/1995 | Sanders et al. |
| 5,438,980 A | 8/1995 | Phillips |
| 5,443,075 A | 8/1995 | Holscher |
| 5,452,714 A | 9/1995 | Anderson et al. |
| 5,492,113 A | 2/1996 | Estes et al. |
| 5,507,282 A | 4/1996 | Younes |
| 5,513,631 A | 5/1996 | McWilliams |
| 5,517,983 A | 5/1996 | Deighan et al. |
| 5,520,071 A | 5/1996 | Jones |
| 5,524,615 A | 6/1996 | Power |
| RE35,295 E | 7/1996 | Estes et al. |
| 5,531,221 A | 7/1996 | Power |
| 5,535,738 A | 7/1996 | Estes et al. |
| 5,540,222 A | 7/1996 | Younes |
| 5,542,415 A | 8/1996 | Brody |
| 5,544,674 A | 8/1996 | Kelly |
| 5,549,106 A | 8/1996 | Gruenke et al. |
| 5,551,418 A | 9/1996 | Estes et al. |
| 5,572,993 A | 11/1996 | Kurome et al. |
| 5,582,163 A | 12/1996 | Bonassa |
| 5,596,984 A | 1/1997 | O'Mahony et al. |
| 5,598,838 A | 2/1997 | Servidio et al. |
| 5,630,411 A | 5/1997 | Holscher |
| 5,632,269 A | 5/1997 | Zdrojkowski |
| 5,632,270 A | 5/1997 | O'Mahony et al. |
| 5,645,048 A | 7/1997 | Brodsky et al. |
| 5,660,171 A | 8/1997 | Kimm et al. |
| 5,664,560 A | 9/1997 | Merrick et al. |
| 5,664,562 A | 9/1997 | Bourdon |
| 5,671,767 A | 9/1997 | Kelly |
| 5,672,041 A | 9/1997 | Ringdahl et al. |
| 5,673,689 A | 10/1997 | Power |
| 5,692,497 A | 12/1997 | Schnitzer et al. |
| 5,694,923 A | 12/1997 | Hete et al. |
| 5,704,345 A | 1/1998 | Berthon-Jones |
| 5,715,812 A | 2/1998 | Deighan et al. |
| 5,720,278 A | 2/1998 | Lachmann et al. |
| 5,735,267 A | 4/1998 | Tobia |
| 5,743,253 A | 4/1998 | Castor et al. |
| 5,752,506 A | 5/1998 | Richardson |
| 5,762,480 A | 6/1998 | Adahan |
| 5,765,558 A | 6/1998 | Psaros et al. |
| 5,771,884 A | 6/1998 | Yarnall et al. |
| 5,782,233 A | 7/1998 | Niemi et al. |
| 5,791,339 A | 8/1998 | Winter |
| 5,794,615 A | 8/1998 | Estes |
| 5,794,986 A | 8/1998 | Gansel et al. |
| 5,803,065 A | 9/1998 | Zdrojkowski et al. |
| 5,813,399 A | 9/1998 | Isaza et al. |
| 5,823,187 A | 10/1998 | Estes et al. |
| 5,826,575 A | 10/1998 | Lail |
| 5,829,441 A | 11/1998 | Kidd et al. |
| 5,864,938 A | 2/1999 | Gansel et al. |
| 5,865,168 A | 2/1999 | Isaza |
| 5,868,133 A | 2/1999 | DeVries et al. |
| 5,878,744 A | 3/1999 | Pfeiffer |
| 5,881,717 A | 3/1999 | Isaza |
| 5,881,723 A | 3/1999 | Wallace et al. |
| 5,884,622 A | 3/1999 | Younes |
| 5,884,623 A | 3/1999 | Winter |
| 5,901,704 A | 5/1999 | Estes et al. |
| 5,904,141 A | 5/1999 | Estes et al. |
| 5,909,731 A | 6/1999 | O'Mahony et al. |
| 5,915,379 A | 6/1999 | Wallace et al. |
| 5,915,380 A | 6/1999 | Wallace et al. |
| 5,915,382 A | 6/1999 | Power |
| 5,918,597 A | 7/1999 | Jones et al. |
| 5,921,238 A | 7/1999 | Bourdon |
| 5,927,274 A | 7/1999 | Servidio et al. |
| 5,934,274 A | 8/1999 | Merrick et al. |
| 5,957,130 A | 9/1999 | Krahbichler et al. |
| 5,970,975 A | 10/1999 | Estes et al. |
| 5,975,081 A | 11/1999 | Hood et al. |
| 6,024,089 A | 2/2000 | Wallace et al. |
| 6,029,664 A | 2/2000 | Zdrojkowski et al. |
| 6,029,665 A | 2/2000 | Berthon-Jones |
| 6,041,777 A | 3/2000 | Faithfull et al. |
| 6,041,780 A | 3/2000 | Richard et al. |
| 6,047,860 A | 4/2000 | Sanders |
| 6,076,523 A | 6/2000 | Jones et al. |
| 6,105,575 A | 8/2000 | Estes et al. |
| 6,116,240 A | 9/2000 | Merrick et al. |
| 6,116,464 A | 9/2000 | Sanders |
| 6,123,073 A | 9/2000 | Schlawin et al. |
| 6,135,105 A | 10/2000 | Lampotang et al. |
| 6,135,106 A | 10/2000 | Dirks et al. |
| 6,142,150 A | 11/2000 | O'Mahony et al. |
| 6,161,539 A | 12/2000 | Winter |
| 6,196,222 B1 | 3/2001 | Heinonen et al. |
| 6,209,540 B1 | 4/2001 | Sugiura et al. |
| 6,213,119 B1 | 4/2001 | Brydon et al. |
| 6,220,245 B1 | 4/2001 | Takabayashi et al. |
| 6,240,919 B1 | 6/2001 | MacDonald et al. |
| 6,253,765 B1 | 7/2001 | Hognelid et al. |
| 6,257,234 B1 | 7/2001 | Sun |
| 6,269,812 B1 | 8/2001 | Wallace et al. |
| 6,273,444 B1 | 8/2001 | Power |
| 6,283,119 B1 | 9/2001 | Bourdon |
| 6,302,105 B1 | 10/2001 | Wickham et al. |
| 6,302,851 B1 | 10/2001 | Gedeon |
| 6,305,372 B1 | 10/2001 | Servidio |
| 6,305,373 B1 | 10/2001 | Wallace et al. |
| 6,305,374 B1 | 10/2001 | Zdrojkowski et al. |
| 6,321,748 B1 | 11/2001 | O'Mahoney |
| 6,325,785 B1 | 12/2001 | Babkes et al. |
| 6,345,619 B1 | 2/2002 | Finn |
| 6,357,438 B1 | 3/2002 | Hansen |
| 6,360,745 B1 | 3/2002 | Wallace et al. |
| 6,369,838 B1 | 4/2002 | Wallace et al. |
| 6,371,113 B1 | 4/2002 | Tobia et al. |

(56) References Cited

U.S. PATENT DOCUMENTS

| | | |
|---|---|---|
| 6,412,483 B1 | 7/2002 | Jones et al. |
| 6,427,689 B1 | 8/2002 | Estes et al. |
| 6,431,169 B1 | 8/2002 | do Val et al. |
| 6,439,229 B1 | 8/2002 | Du et al. |
| 6,467,477 B1 | 10/2002 | Frank et al. |
| 6,467,478 B1 | 10/2002 | Merrick et al. |
| 6,484,719 B1 | 11/2002 | Berthon-Jones |
| 6,526,970 B2 | 3/2003 | DeVries et al. |
| 6,532,956 B2 | 3/2003 | Hill |
| 6,532,957 B2 | 3/2003 | Berthon-Jones |
| 6,539,940 B2 | 4/2003 | Zdrojkowski et al. |
| 6,546,930 B1 | 4/2003 | Emerson et al. |
| 6,553,991 B1 | 4/2003 | Isaza |
| 6,553,992 B1 | 4/2003 | Berthon-Jones et al. |
| 6,557,553 B1 | 5/2003 | Borrello |
| 6,557,554 B1 | 5/2003 | Sugiura |
| 6,571,795 B2 | 6/2003 | Bourdon |
| 6,575,163 B1 | 6/2003 | Berthon-Jones |
| 6,578,575 B1 | 6/2003 | Jonson |
| 6,581,597 B2 | 6/2003 | Sugiura |
| 6,588,422 B1 | 7/2003 | Berthon-Jones et al. |
| 6,595,213 B2 | 7/2003 | Bennarsten |
| 6,609,517 B1 | 8/2003 | Estes et al. |
| 6,612,995 B2 | 9/2003 | Leonhardt et al. |
| 6,622,726 B1 | 9/2003 | Du |
| 6,626,175 B2 | 9/2003 | Jafari et al. |
| 6,629,527 B1 | 10/2003 | Estes et al. |
| 6,629,934 B2 | 10/2003 | Mault et al. |
| 6,631,716 B1 | 10/2003 | Robinson et al. |
| 6,640,806 B2 | 11/2003 | Yurko |
| 6,644,310 B1 | 11/2003 | Delache et al. |
| 6,651,657 B1 | 11/2003 | Manigel et al. |
| 6,668,824 B1 | 12/2003 | Isaza et al. |
| 6,672,300 B1 | 1/2004 | Grant |
| 6,675,797 B1 | 1/2004 | Berthon-Jones |
| 6,675,801 B2 | 1/2004 | Wallace et al. |
| 6,679,258 B1 | 1/2004 | Strom |
| 6,688,307 B2 | 2/2004 | Berthon-Jones |
| 6,708,691 B1 | 3/2004 | Hayek |
| 6,718,974 B1 | 4/2004 | Moberg |
| 6,725,447 B1 | 4/2004 | Gilman et al. |
| 6,739,337 B2 | 5/2004 | Isaza |
| 6,755,193 B2 | 6/2004 | Berthon-Jones et al. |
| 6,758,217 B1 | 7/2004 | Younes |
| 6,761,167 B2 | 7/2004 | Nadjafizadeh et al. |
| 6,761,168 B1 | 7/2004 | Nadjafizadeh et al. |
| 6,796,305 B1 | 9/2004 | Banner et al. |
| 6,810,876 B2 | 11/2004 | Berthon-Jones |
| 6,814,074 B1 | 11/2004 | Nadjafizadeh et al. |
| 6,820,613 B2 | 11/2004 | Wenkebach |
| 6,823,866 B2 | 11/2004 | Jafari et al. |
| 6,837,242 B2 | 1/2005 | Younes |
| 6,837,244 B2 | 1/2005 | Yagi et al. |
| 6,854,462 B2 | 2/2005 | Berthon-Jones et al. |
| 6,860,858 B2 | 3/2005 | Green et al. |
| 6,866,040 B1 | 3/2005 | Bourdon |
| 6,877,511 B2 | 4/2005 | DeVries. et al. |
| 6,899,103 B1 | 5/2005 | Hood et al. |
| 6,910,480 B1 | 6/2005 | Berthon-Jones |
| 6,915,803 B2 | 7/2005 | Berthon-Jones et al. |
| 6,920,878 B2 | 7/2005 | Sinderby et al. |
| 6,932,084 B2 | 8/2005 | Estes et al. |
| 6,948,497 B2 | 9/2005 | Zdrojkowski et al. |
| 6,960,854 B2 | 11/2005 | Nadjafizadeh et al. |
| 6,976,487 B1 | 12/2005 | Melker et al. |
| 6,997,881 B2 | 2/2006 | Green et al. |
| 7,000,610 B2 | 2/2006 | Bennarsten et al. |
| 7,000,612 B2 | 2/2006 | Jafari et al. |
| 7,013,892 B2 | 3/2006 | Estes et al. |
| 7,021,310 B1 | 4/2006 | Sinderby et al. |
| 7,032,589 B2 | 4/2006 | Kerechanin, II et al. |
| 7,036,504 B2 | 5/2006 | Wallace et al. |
| 7,040,321 B2 | 5/2006 | Göbel |
| 7,055,522 B2 | 6/2006 | Berthon-Jones |
| 7,066,173 B2 | 6/2006 | Banner et al. |
| 7,077,131 B2 | 7/2006 | Hansen |
| RE39,225 E | 8/2006 | Isaza et al. |
| 7,096,866 B2 | 8/2006 | Be'eri et al. |
| 7,100,607 B2 | 9/2006 | Zdrojkowski et al. |
| 7,100,609 B2 | 9/2006 | Berthon-Jones et al. |
| 7,117,438 B2 | 10/2006 | Wallace et al. |
| 7,137,389 B2 | 11/2006 | Berthon-Jones |
| 7,152,598 B2 | 12/2006 | Morris et al. |
| 7,162,296 B2 | 1/2007 | Leonhardt et al. |
| 7,210,478 B2 | 5/2007 | Banner et al. |
| 7,225,013 B2 | 5/2007 | Geva et al. |
| 7,246,618 B2 | 7/2007 | Habashi |
| 7,255,103 B2 | 8/2007 | Bassin |
| 7,267,121 B2 | 9/2007 | Ivri |
| 7,270,126 B2 | 9/2007 | Wallace et al. |
| 7,270,128 B2 | 9/2007 | Berthon-Jones et al. |
| 7,296,573 B2 | 11/2007 | Estes et al. |
| 7,305,987 B2 | 12/2007 | Schöller et al. |
| 7,305,988 B2 | 12/2007 | Acker |
| 7,320,320 B2 | 1/2008 | Berthon-Jones |
| 7,334,578 B2 | 2/2008 | Biondi et al. |
| 7,367,337 B2 | 5/2008 | Berthon-Jones et al. |
| 7,369,757 B2 | 5/2008 | Farbarik |
| 7,370,650 B2 | 5/2008 | Nadjafizadeh et al. |
| RE40,402 E | 6/2008 | Leonhardt et al. |
| 7,425,201 B2 | 9/2008 | Euliano |
| 7,428,902 B2 | 9/2008 | Du et al. |
| 7,455,717 B2 | 11/2008 | Sprinkle |
| 7,460,959 B2 | 12/2008 | Jafari |
| 7,475,685 B2 | 1/2009 | Dietz et al. |
| 7,484,508 B2 | 2/2009 | Younes |
| 7,487,773 B2 | 2/2009 | Li |
| 7,509,957 B2 | 3/2009 | Duquette et al. |
| 7,516,742 B2 | 4/2009 | Stenzler et al. |
| 7,520,279 B2 | 4/2009 | Berthon-Jones |
| 7,533,670 B1 | 5/2009 | Freitag et al. |
| 7,556,038 B2 | 7/2009 | Kirby et al. |
| 7,588,031 B2 | 9/2009 | Truschel et al. |
| 7,588,543 B2 | 9/2009 | Euliano |
| 7,610,914 B2 | 11/2009 | Bolam et al. |
| 7,617,824 B2 | 11/2009 | Doyle |
| 7,621,270 B2 | 11/2009 | Morris et al. |
| 7,621,271 B2 | 11/2009 | Brugnoli |
| 7,644,713 B2 | 1/2010 | Berthon-Jones |
| 7,654,802 B2 | 2/2010 | Crawford, Jr. et al. |
| 7,672,720 B2 | 3/2010 | Heath |
| 7,678,058 B2 | 3/2010 | Patangay et al. |
| 7,678,061 B2 | 3/2010 | Lee et al. |
| 7,682,312 B2 | 3/2010 | Lurie |
| 7,690,378 B1 | 4/2010 | Turcott |
| 7,694,677 B2 | 4/2010 | Tang |
| 7,697,990 B2 | 4/2010 | Ujhazy et al. |
| 7,708,016 B2 | 5/2010 | Zaiser et al. |
| 7,717,110 B2 | 5/2010 | Kane et al. |
| 7,717,111 B2 | 5/2010 | Schneider et al. |
| 7,717,113 B2 | 5/2010 | Andrieux |
| 7,722,546 B2 | 5/2010 | Madaus et al. |
| D618,356 S | 6/2010 | Ross |
| 7,727,160 B2 | 6/2010 | Green et al. |
| 7,730,886 B2 | 6/2010 | Berthon-Jones |
| 7,751,894 B1 | 7/2010 | Freeberg |
| 7,763,097 B2 | 7/2010 | Federspiel et al. |
| 7,770,578 B2 | 8/2010 | Estes et al. |
| 7,784,461 B2 | 8/2010 | Figueiredo et al. |
| 7,793,659 B2 | 9/2010 | Breen |
| 7,802,571 B2 | 9/2010 | Tehrani |
| 7,810,496 B2 | 10/2010 | Estes et al. |
| 7,810,497 B2 | 10/2010 | Pittman et al. |
| 7,819,815 B2 | 10/2010 | Younes |
| 7,823,588 B2 | 11/2010 | Hansen |
| 7,841,343 B2 | 11/2010 | Deane |
| 7,849,854 B2 | 12/2010 | DeVries et al. |
| 7,855,716 B2 | 12/2010 | McCreary et al. |
| 7,866,318 B2 | 1/2011 | Bassin |
| 7,874,293 B2 | 1/2011 | Gunaratnam et al. |
| D632,796 S | 2/2011 | Ross et al. |
| D632,797 S | 2/2011 | Ross et al. |
| 7,891,354 B2 | 2/2011 | Farbarik |
| 7,893,560 B2 | 2/2011 | Carter |

(56) References Cited

U.S. PATENT DOCUMENTS

| | | |
|---|---|---|
| 7,914,459 B2 | 3/2011 | Green et al. |
| D638,852 S | 5/2011 | Skidmore et al. |
| 7,934,499 B2 | 5/2011 | Berthon-Jones |
| 7,984,714 B2 | 7/2011 | Hausmann et al. |
| D643,535 S | 8/2011 | Ross et al. |
| 7,992,557 B2 | 8/2011 | Nadjafizadeh et al. |
| 8,001,967 B2 | 8/2011 | Wallace et al. |
| D645,158 S | 9/2011 | Sanchez et al. |
| 8,015,974 B2 | 9/2011 | Christopher |
| 8,020,556 B2 * | 9/2011 | Hayek ................ A61M 16/06 128/207.14 |
| 8,021,310 B2 | 9/2011 | Sanborn et al. |
| D649,157 S | 11/2011 | Skidmore et al. |
| D652,521 S | 1/2012 | Ross et al. |
| D652,936 S | 1/2012 | Ross et al. |
| D653,749 S | 2/2012 | Winter et al. |
| 8,113,062 B2 | 2/2012 | Graboi et al. |
| 8,122,885 B2 | 2/2012 | Berthon-Jones |
| D655,405 S | 3/2012 | Winter et al. |
| D655,809 S | 3/2012 | Winter et al. |
| D656,237 S | 3/2012 | Sanchez et al. |
| 8,136,521 B2 | 3/2012 | Matthews |
| 8,181,648 B2 | 5/2012 | Perine et al. |
| 8,210,173 B2 | 7/2012 | Vandine |
| 8,210,174 B2 | 7/2012 | Farbarik |
| 8,240,684 B2 | 8/2012 | Ross et al. |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 8,347,883 B2 * | 1/2013 | Bird ................ A61M 16/0858 128/203.15 |
| 8,353,844 B2 | 1/2013 | Jin Wei |
| 8,408,203 B2 * | 4/2013 | Tham ................ A61M 16/024 128/200.14 |
| D692,556 S | 10/2013 | Winter |
| D693,001 S | 11/2013 | Winter |
| 8,603,006 B2 | 12/2013 | Mulqueeny et al. |
| 8,617,083 B2 | 12/2013 | Euliano |
| 8,646,447 B2 | 2/2014 | Martin |
| D701,601 S | 3/2014 | Winter |
| 8,672,858 B2 | 3/2014 | Euliano |
| 8,689,791 B2 * | 4/2014 | Hayek ................ A61M 16/20 128/207.14 |
| 8,826,907 B2 | 9/2014 | Masic |
| 8,876,728 B2 | 11/2014 | Baloa Welzien |
| 8,910,632 B2 | 12/2014 | Tiedje |
| 8,920,333 B2 | 12/2014 | Younes |
| 8,950,399 B2 | 2/2015 | Handzsuj |
| 8,960,192 B2 | 2/2015 | Welzien et al. |
| D731,048 S | 6/2015 | Winter |
| D731,049 S | 6/2015 | Winter |
| D731,065 S | 6/2015 | Winter |
| D736,905 S | 8/2015 | Winter |
| 9,155,852 B2 | 10/2015 | Soliman et al. |
| D744,095 S | 11/2015 | Winter |
| 9,220,856 B2 | 12/2015 | Martin |
| 9,392,964 B2 | 7/2016 | Mulqueeny |
| 9,592,356 B2 | 3/2017 | Truschel |
| 9,808,591 B2 | 11/2017 | Esmaeil-zadeh-azar |
| 9,839,760 B2 | 12/2017 | Bonassa |
| 9,895,083 B2 | 2/2018 | Zheng |
| 9,925,346 B2 | 3/2018 | Dong et al. |
| 9,950,129 B2 | 4/2018 | Glenn et al. |
| 9,956,363 B2 | 5/2018 | Masic |
| 9,987,457 B2 | 6/2018 | Winter et al. |
| 10,022,084 B2 | 7/2018 | Nonaka |
| 10,165,966 B2 | 1/2019 | Banner |
| 10,207,068 B2 | 2/2019 | Jafari et al. |
| 10,293,126 B2 | 5/2019 | Berry |
| 10,668,239 B2 | 6/2020 | Kimm |
| 2005/0034727 A1 | 2/2005 | Shusterman et al. |
| 2005/0039748 A1 | 2/2005 | Andrieux |
| 2005/0139212 A1 | 6/2005 | Bourdon |
| 2005/0205093 A1 * | 9/2005 | Jabour ................ A61M 16/021 128/204.23 |
| 2006/0155336 A1 | 7/2006 | Heath |
| 2006/0174884 A1 | 8/2006 | Habashi |
| 2006/0235324 A1 | 10/2006 | Lynn |
| 2006/0249148 A1 | 11/2006 | Younes |
| 2006/0278223 A1 | 12/2006 | Younes |
| 2007/0000494 A1 | 1/2007 | Banner et al. |
| 2007/0017515 A1 | 1/2007 | Wallace et al. |
| 2007/0028921 A1 | 2/2007 | Banner et al. |
| 2007/0044796 A1 | 3/2007 | Zdrojkowski et al. |
| 2007/0044799 A1 | 3/2007 | Hete et al. |
| 2007/0056588 A1 * | 3/2007 | Hayek ................ A61M 16/06 128/205.25 |
| 2007/0077200 A1 | 4/2007 | Baker |
| 2007/0215146 A1 | 9/2007 | Douglas et al. |
| 2007/0227537 A1 | 10/2007 | Bemister et al. |
| 2007/0272241 A1 | 11/2007 | Sanborn et al. |
| 2007/0284361 A1 | 12/2007 | Nadjafizadeh et al. |
| 2008/0011301 A1 | 1/2008 | Qian |
| 2008/0017198 A1 | 1/2008 | Ivri |
| 2008/0045813 A1 | 2/2008 | Phuah et al. |
| 2008/0053441 A1 | 3/2008 | Gottlib et al. |
| 2008/0053443 A1 | 3/2008 | Estes et al. |
| 2008/0053444 A1 | 3/2008 | Estes et al. |
| 2008/0072896 A1 | 3/2008 | Setzer et al. |
| 2008/0072901 A1 | 3/2008 | Habashi |
| 2008/0072902 A1 | 3/2008 | Setzer et al. |
| 2008/0078390 A1 | 4/2008 | Milne et al. |
| 2008/0083644 A1 | 4/2008 | Janbakhsh et al. |
| 2008/0092894 A1 | 4/2008 | Nicolazzi et al. |
| 2008/0097234 A1 | 4/2008 | Nicolazzi et al. |
| 2008/0110461 A1 | 5/2008 | Mulqueeny et al. |
| 2008/0142012 A1 | 6/2008 | Farnsworth et al. |
| 2008/0163872 A1 | 7/2008 | Negele et al. |
| 2008/0185002 A1 | 8/2008 | Berthon-Jones et al. |
| 2008/0196720 A1 | 8/2008 | Kollmeyer et al. |
| 2008/0202528 A1 | 8/2008 | Carter et al. |
| 2008/0216832 A1 | 9/2008 | Carter et al. |
| 2008/0216833 A1 | 9/2008 | Pujol et al. |
| 2008/0234595 A1 | 9/2008 | Ranieri et al. |
| 2008/0257349 A1 | 10/2008 | Hedner et al. |
| 2008/0283061 A1 | 11/2008 | Tiedje |
| 2008/0295839 A1 | 12/2008 | Habashi |
| 2009/0020120 A1 | 1/2009 | Schatzl et al. |
| 2009/0020121 A1 | 1/2009 | Bassin |
| 2009/0038616 A1 | 2/2009 | Mulcahy et al. |
| 2009/0056719 A1 | 3/2009 | Newman, Jr. |
| 2009/0084371 A1 | 4/2009 | DeVries et al. |
| 2009/0095298 A1 | 4/2009 | Gunaratnam et al. |
| 2009/0107502 A1 | 4/2009 | Younes |
| 2009/0114224 A1 | 5/2009 | Handzsuj et al. |
| 2009/0159082 A1 | 6/2009 | Eger |
| 2009/0165795 A1 | 7/2009 | Nadjafizadeh et al. |
| 2009/0171176 A1 | 7/2009 | Andersohn |
| 2009/0173347 A1 | 7/2009 | Berthon-Jones |
| 2009/0188502 A1 | 7/2009 | Tiedje |
| 2009/0199855 A1 | 8/2009 | Davenport |
| 2009/0205661 A1 | 8/2009 | Stephenson et al. |
| 2009/0205663 A1 | 8/2009 | Vandine et al. |
| 2009/0221926 A1 | 9/2009 | Younes |
| 2009/0229611 A1 | 9/2009 | Martin et al. |
| 2009/0241951 A1 | 10/2009 | Jafari et al. |
| 2009/0241952 A1 | 10/2009 | Nicolazzi et al. |
| 2009/0241953 A1 | 10/2009 | Vandine et al. |
| 2009/0241955 A1 | 10/2009 | Jafari et al. |
| 2009/0241956 A1 | 10/2009 | Baker, Jr. et al. |
| 2009/0241957 A1 | 10/2009 | Baker, Jr. |
| 2009/0241958 A1 | 10/2009 | Baker, Jr. |
| 2009/0241962 A1 | 10/2009 | Jafari et al. |
| 2009/0247848 A1 | 10/2009 | Baker, Jr. |
| 2009/0247849 A1 | 10/2009 | McCutcheon et al. |
| 2009/0247853 A1 | 10/2009 | Debreczeny |
| 2009/0247891 A1 | 10/2009 | Wood |
| 2009/0287070 A1 | 11/2009 | Baker, Jr. |
| 2009/0301486 A1 | 12/2009 | Masic |
| 2009/0301487 A1 | 12/2009 | Masic |
| 2009/0301490 A1 | 12/2009 | Masic |
| 2009/0301491 A1 | 12/2009 | Masic et al. |

(56) References Cited

U.S. PATENT DOCUMENTS

| | | |
|---|---|---|
| 2010/0011307 A1 | 1/2010 | Desfossez et al. |
| 2010/0024820 A1 | 2/2010 | Bourdon |
| 2010/0051026 A1 | 3/2010 | Graboi |
| 2010/0051029 A1 | 3/2010 | Jafari et al. |
| 2010/0065055 A1 | 3/2010 | Morris et al. |
| 2010/0065057 A1 | 3/2010 | Berthon-Jones |
| 2010/0069761 A1 | 3/2010 | Karst et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0078017 A1 | 4/2010 | Andrieux et al. |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0137380 A1 | 6/2010 | Maybaum |
| 2010/0137723 A1 | 6/2010 | Patangay et al. |
| 2010/0137729 A1 | 6/2010 | Pierry et al. |
| 2010/0137730 A1 | 6/2010 | Hatlestad |
| 2010/0139660 A1 | 6/2010 | Adahan |
| 2010/0145201 A1 | 6/2010 | Westbrook et al. |
| 2010/0147303 A1 | 6/2010 | Jafari et al. |
| 2010/0152553 A1 | 6/2010 | Ujhazy et al. |
| 2010/0152560 A1 | 6/2010 | Turcott |
| 2010/0170512 A1 | 7/2010 | Kuypers et al. |
| 2010/0174200 A1 | 7/2010 | Wood et al. |
| 2010/0174207 A1 | 7/2010 | Lee et al. |
| 2010/0180898 A1 | 7/2010 | Schneider et al. |
| 2010/0186741 A1 | 7/2010 | Aylsworth et al. |
| 2010/0186742 A1 | 7/2010 | Sherman et al. |
| 2010/0186743 A1 | 7/2010 | Kane et al. |
| 2010/0186744 A1 | 7/2010 | Andrieux |
| 2010/0191076 A1 | 7/2010 | Lewicke et al. |
| 2010/0191137 A1 | 7/2010 | Brada et al. |
| 2010/0192094 A1 | 7/2010 | Jeha et al. |
| 2010/0198086 A1 | 8/2010 | Kuo et al. |
| 2010/0199991 A1 | 8/2010 | Koledin |
| 2010/0210924 A1 | 8/2010 | Parthasarathy et al. |
| 2010/0218764 A1 | 9/2010 | Kwok et al. |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0218773 A1 | 9/2010 | Thornton |
| 2010/0222692 A1 | 9/2010 | McCawley et al. |
| 2010/0224190 A1 | 9/2010 | Tilley et al. |
| 2010/0228133 A1 | 9/2010 | Averina et al. |
| 2010/0228134 A1 | 9/2010 | Martikka et al. |
| 2010/0229863 A1 | 9/2010 | Enk |
| 2010/0234750 A1 | 9/2010 | Ariav et al. |
| 2010/0236553 A1 | 9/2010 | Jafari et al. |
| 2010/0236554 A1 | 9/2010 | Prete |
| 2010/0236555 A1 | 9/2010 | Jafari et al. |
| 2010/0241009 A1 | 9/2010 | Petkie |
| 2010/0242961 A1 | 9/2010 | Mougel et al. |
| 2010/0242965 A1 | 9/2010 | Berthon-Jones |
| 2010/0249549 A1 | 9/2010 | Baker, Jr. et al. |
| 2010/0249630 A1 | 9/2010 | Droitcour et al. |
| 2010/0249631 A1 | 9/2010 | Aoki et al. |
| 2010/0249632 A1 | 9/2010 | Lee et al. |
| 2010/0249633 A1 | 9/2010 | Droitcour et al. |
| 2010/0252037 A1 | 10/2010 | Wondka et al. |
| 2010/0252039 A1 | 10/2010 | Cipollone et al. |
| 2010/0252040 A1 | 10/2010 | Kapust et al. |
| 2010/0252041 A1 | 10/2010 | Kapust et al. |
| 2010/0252042 A1 | 10/2010 | Kapust et al. |
| 2010/0252043 A1 | 10/2010 | Freitag |
| 2010/0256463 A1 | 10/2010 | Greenwald et al. |
| 2010/0258116 A1 | 10/2010 | Federspiel et al. |
| 2010/0258124 A1 | 10/2010 | Madaus et al. |
| 2010/0258126 A1 | 10/2010 | Ujhazy et al. |
| 2010/0258127 A1 | 10/2010 | Hk |
| 2010/0262032 A1 | 10/2010 | Freeberg |
| 2010/0275920 A1* | 11/2010 | Tham ............... A61M 16/0051 128/204.23 |
| 2010/0282259 A1 | 11/2010 | Figueiredo et al. |
| 2010/0288279 A1 | 11/2010 | Seiver et al. |
| 2010/0288283 A1 | 11/2010 | Campbell et al. |
| 2010/0300446 A1 | 12/2010 | Nicolazzi et al. |
| 2010/0307499 A1 | 12/2010 | Eger et al. |
| 2011/0011400 A1 | 1/2011 | Gentner et al. |
| 2011/0017214 A1 | 1/2011 | Tehrani |
| 2011/0023878 A1 | 2/2011 | Thiessen |
| 2011/0023879 A1 | 2/2011 | Vandine et al. |
| 2011/0023880 A1 | 2/2011 | Thiessen |
| 2011/0023881 A1 | 2/2011 | Thiessen |
| 2011/0029910 A1 | 2/2011 | Thiessen |
| 2011/0036352 A1 | 2/2011 | Estes et al. |
| 2011/0041849 A1 | 2/2011 | Chen et al. |
| 2011/0041850 A1 | 2/2011 | Vandine et al. |
| 2011/0126829 A1 | 6/2011 | Carter et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0128008 A1 | 6/2011 | Carter |
| 2011/0132361 A1 | 6/2011 | Sanchez |
| 2011/0132362 A1 | 6/2011 | Sanchez |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0132367 A1 | 6/2011 | Patel |
| 2011/0132368 A1 | 6/2011 | Sanchez et al. |
| 2011/0132369 A1 | 6/2011 | Sanchez |
| 2011/0132371 A1 | 6/2011 | Sanchez et al. |
| 2011/0133936 A1 | 6/2011 | Sanchez et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138315 A1 | 6/2011 | Vandine et al. |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0154241 A1 | 6/2011 | Skidmore et al. |
| 2011/0175728 A1 | 7/2011 | Baker, Jr. |
| 2011/0196251 A1 | 8/2011 | Jourdain et al. |
| 2011/0197888 A1 | 8/2011 | Deutsch et al. |
| 2011/0209702 A1 | 9/2011 | Vuong et al. |
| 2011/0209704 A1 | 9/2011 | Jafari et al. |
| 2011/0209707 A1 | 9/2011 | Terhark |
| 2011/0213215 A1 | 9/2011 | Doyle et al. |
| 2011/0230780 A1 | 9/2011 | Sanborn et al. |
| 2011/0249006 A1 | 10/2011 | Wallace et al. |
| 2011/0259330 A1 | 10/2011 | Jafari et al. |
| 2011/0259332 A1 | 10/2011 | Sanchez et al. |
| 2011/0259333 A1 | 10/2011 | Sanchez et al. |
| 2011/0265024 A1 | 10/2011 | Leone et al. |
| 2011/0271960 A1 | 11/2011 | Milne et al. |
| 2011/0273299 A1 | 11/2011 | Milne et al. |
| 2012/0000467 A1 | 1/2012 | Milne et al. |
| 2012/0000468 A1 | 1/2012 | Milne et al. |
| 2012/0000469 A1 | 1/2012 | Milne et al. |
| 2012/0000470 A1 | 1/2012 | Milne et al. |
| 2012/0029317 A1 | 2/2012 | Doyle et al. |
| 2012/0030611 A1 | 2/2012 | Skidmore |
| 2012/0060841 A1 | 3/2012 | Crawford, Jr. et al. |
| 2012/0071729 A1 | 3/2012 | Doyle et al. |
| 2012/0090611 A1 | 4/2012 | Graboi et al. |
| 2012/0096381 A1 | 4/2012 | Milne et al. |
| 2012/0133519 A1 | 5/2012 | Milne et al. |
| 2012/0136222 A1 | 5/2012 | Doyle et al. |
| 2012/0137249 A1 | 5/2012 | Milne et al. |
| 2012/0137250 A1 | 5/2012 | Milne et al. |
| 2012/0157872 A1 | 6/2012 | Welzien et al. |
| 2012/0167885 A1 | 7/2012 | Masic et al. |
| 2012/0185792 A1 | 7/2012 | Kimm et al. |
| 2012/0192869 A1* | 8/2012 | Hayek ............... A61M 16/06 128/205.24 |
| 2012/0197578 A1 | 8/2012 | Vig et al. |
| 2012/0197580 A1 | 8/2012 | Vij et al. |
| 2012/0211008 A1 | 8/2012 | Perine et al. |
| 2012/0216809 A1 | 8/2012 | Milne et al. |
| 2012/0216810 A1 | 8/2012 | Jafari et al. |

(56) References Cited

U.S. PATENT DOCUMENTS

| | | |
|---|---|---|
| 2012/0216811 A1 | 8/2012 | Kimm et al. |
| 2012/0226444 A1 | 9/2012 | Milne et al. |
| 2012/0247471 A1 | 10/2012 | Masic et al. |
| 2012/0272960 A1 | 11/2012 | Milne |
| 2012/0272961 A1 | 11/2012 | Masic et al. |
| 2012/0272962 A1 | 11/2012 | Doyle et al. |
| 2012/0277616 A1 | 11/2012 | Sanborn et al. |
| 2012/0279501 A1 | 11/2012 | Wallace et al. |
| 2012/0304995 A1 | 12/2012 | Kauc |
| 2012/0304997 A1 | 12/2012 | Jafari et al. |
| 2013/0000644 A1 | 1/2013 | Thiessen |
| 2013/0006133 A1 | 1/2013 | Doyle et al. |
| 2013/0006134 A1 | 1/2013 | Doyle et al. |
| 2013/0008443 A1 | 1/2013 | Thiessen |
| 2013/0025596 A1 | 1/2013 | Jafari et al. |
| 2013/0025597 A1 | 1/2013 | Doyle et al. |
| 2013/0032151 A1 | 2/2013 | Adahan |
| 2013/0042869 A1 | 2/2013 | Andrieux et al. |
| 2013/0047983 A1 | 2/2013 | Andrieux et al. |
| 2013/0047989 A1 | 2/2013 | Vandine et al. |
| 2013/0053717 A1 | 2/2013 | Vandine et al. |
| 2013/0074844 A1 | 3/2013 | Kimm et al. |
| 2013/0081536 A1 | 4/2013 | Crawford, Jr. et al. |
| 2013/0104896 A1 | 5/2013 | Kimm et al. |
| 2013/0146055 A1 | 6/2013 | Jafari et al. |
| 2013/0152923 A1 | 6/2013 | Andrieux et al. |
| 2013/0158370 A1 | 6/2013 | Doyle et al. |
| 2013/0159912 A1 | 6/2013 | Baker, Jr. |
| 2013/0167842 A1 | 7/2013 | Jafari et al. |
| 2013/0167843 A1 | 7/2013 | Kimm et al. |
| 2013/0174846 A1 | 7/2013 | Stenqvist |
| 2013/0186397 A1 | 7/2013 | Patel |
| 2013/0186400 A1 | 7/2013 | Jafari et al. |
| 2013/0186401 A1 | 7/2013 | Jafari et al. |
| 2013/0192599 A1 | 8/2013 | Nakai et al. |
| 2013/0220324 A1 | 8/2013 | Jafari et al. |
| 2013/0233314 A1 | 9/2013 | Jafari et al. |
| 2013/0233319 A1 | 9/2013 | Winter et al. |
| 2013/0239038 A1 | 9/2013 | Skidmore et al. |
| 2013/0239967 A1 | 9/2013 | Jafari et al. |
| 2013/0255682 A1 | 10/2013 | Jafari et al. |
| 2013/0255685 A1 | 10/2013 | Jafari et al. |
| 2013/0276788 A1 | 10/2013 | Masic |
| 2013/0283197 A1 | 10/2013 | Skidmore |
| 2013/0284172 A1 | 10/2013 | Doyle et al. |
| 2013/0284173 A1 | 10/2013 | Masic et al. |
| 2013/0284177 A1 | 10/2013 | Li et al. |
| 2013/0327331 A1 | 12/2013 | Bourdon |
| 2013/0333697 A1 | 12/2013 | Carter et al. |
| 2013/0333703 A1 | 12/2013 | Wallace et al. |
| 2013/0338514 A1 | 12/2013 | Karst et al. |
| 2013/0345532 A1 | 12/2013 | Doyle et al. |
| 2014/0000606 A1 | 1/2014 | Doyle et al. |
| 2014/0012150 A1 | 1/2014 | Milne et al. |
| 2014/0034054 A1 | 2/2014 | Angelico et al. |
| 2014/0034056 A1 | 2/2014 | Leone et al. |
| 2014/0041656 A1 | 2/2014 | Jourdain et al. |
| 2014/0048071 A1 | 2/2014 | Milne et al. |
| 2014/0048072 A1 | 2/2014 | Angelico et al. |
| 2014/0121553 A1 | 5/2014 | Milne et al. |
| 2014/0123979 A1 | 5/2014 | Doyle et al. |
| 2014/0130798 A1 | 5/2014 | Milne et al. |
| 2014/0182590 A1 | 7/2014 | Platt et al. |
| 2014/0224250 A1 | 8/2014 | Sanchez et al. |
| 2014/0251328 A1 | 9/2014 | Graboi et al. |
| 2014/0261409 A1 | 9/2014 | Dong et al. |
| 2014/0261410 A1 | 9/2014 | Sanchez et al. |
| 2014/0261424 A1 | 9/2014 | Doyle et al. |
| 2014/0276176 A1 | 9/2014 | Winter |
| 2014/0290657 A1 | 10/2014 | Vandine et al. |
| 2014/0309507 A1 | 10/2014 | Baker, Jr. |
| 2014/0345616 A1 | 11/2014 | Masic |
| 2014/0360497 A1 | 12/2014 | Jafari et al. |
| 2014/0366879 A1 | 12/2014 | Kimm et al. |
| 2014/0373845 A1 | 12/2014 | Dong |
| 2015/0034082 A1 | 2/2015 | Kimm et al. |
| 2015/0045687 A1 | 2/2015 | Nakai et al. |
| 2015/0090258 A1 | 4/2015 | Milne et al. |
| 2015/0090264 A1 | 4/2015 | Dong |
| 2015/0107584 A1 | 4/2015 | Jafari et al. |
| 2015/0217069 A1 | 8/2015 | Novotni et al. |
| 2015/0231351 A1 | 8/2015 | Jonson |
| 2016/0045694 A1 | 2/2016 | Esmaeil-zadeh-azar |
| 2016/0106938 A1 | 4/2016 | Jourdain et al. |
| 2016/0114115 A1 | 4/2016 | Glenn et al. |
| 2016/0135713 A1 | 5/2016 | Chbat et al. |
| 2016/0243324 A1 | 8/2016 | Doyle et al. |
| 2016/0250427 A1 | 9/2016 | Jafari et al. |
| 2016/0256643 A1 | 9/2016 | Graboi et al. |
| 2016/0256656 A1 | 9/2016 | Glenn et al. |
| 2016/0354566 A1 | 12/2016 | Thiessen |
| 2017/0095627 A1 | 4/2017 | Jafari et al. |
| 2017/0164872 A1 | 6/2017 | Sanborn et al. |
| 2017/0182269 A1 | 6/2017 | Masic et al. |
| 2017/0296765 A1 | 10/2017 | Dong et al. |
| 2018/0036500 A1 | 2/2018 | Esmaeil-zadeh-azar |
| 2018/0193578 A1 | 7/2018 | Glenn et al. |
| 2018/0207378 A1 | 7/2018 | Masic |
| 2018/0207379 A1 | 7/2018 | Masic |
| 2018/0256838 A1 | 9/2018 | Doyle et al. |
| 2018/0304034 A1 | 10/2018 | Vicario et al. |
| 2019/0143058 A1 | 5/2019 | Kimm |

FOREIGN PATENT DOCUMENTS

| | | |
|---|---|---|
| EP | 858352 | 1/2005 |
| EP | 1515767 | 8/2009 |
| JP | 2000175886 | 6/2000 |
| JP | 2008000436 | 1/2008 |
| JP | 2008178695 | 8/2008 |
| JP | 5608675 | 10/2014 |
| JP | 5858927 | 2/2016 |
| WO | 9014852 | 12/1990 |
| WO | 9214505 | 9/1992 |
| WO | 9308857 | 5/1993 |
| WO | 199715343 | 5/1997 |
| WO | 9812965 | 4/1998 |
| WO | 199951292 | 10/1999 |
| WO | 199962580 | 12/1999 |
| WO | 2000/10634 | 3/2000 |
| WO | 200078380 | 12/2000 |
| WO | 01/00264 | 1/2001 |
| WO | 01/00265 | 1/2001 |
| WO | 200174430 | 10/2001 |
| WO | 2002028460 | 4/2002 |
| WO | 2002032488 | 4/2002 |
| WO | 2003008027 | 1/2003 |
| WO | 4047621 | 6/2004 |
| WO | 2005004780 | 1/2005 |
| WO | 2007082384 | 7/2007 |
| WO | 2007102866 | 9/2007 |
| WO | 2007145948 | 12/2007 |
| WO | 2010081223 | 7/2010 |
| WO | 2010121313 | 10/2010 |
| WO | 2011145014 | 11/2011 |
| WO | 2013137797 | 9/2013 |
| WO | 2016189069 | 12/2016 |
| WO | 2017055959 | 4/2017 |

OTHER PUBLICATIONS

Puritan Bennett 980 Series Ventilator Operator's Manual, Covidien, Jan. 29, 2014, Part. No. 10077893 A Jan. 2014, 506 pages.
Canadian Office Action in Application 3046571, dated Nov. 6, 2019, 4 pages.
PCT International Preliminary Report on Patentability in International Application PCT/US2018/058226, dated May 19, 2020, 9 pages.
7200 Series Ventilator, Options, and Accessories: Operator's Manual. Nellcor Puritan Bennett, Part No. 22300 A, Sep. 1990, pp. 1-196.
7200 Ventilatory System: Addendum/Errata. Nellcor Puritan Bennett, Part No. 4-023576-00, Rev. A, Apr. 1998, pp. 1-32.

(56) References Cited

OTHER PUBLICATIONS

800 Operator's and Technical Reference Manual. Series Ventilator System, Nellcor Puritan Bennett, Part No. 4-070088-00, Rev. L, Aug. 2010, pp. 1-476.
840 Operator's and Technical Reference Manual. Ventilator System, Nellcor Puritan Bennett, Part No. 4-075609-00, Rev. G, Oct. 2006, pp. 1-424.
Amato, Marcelo et al., "Driving Pressure and Survival in the Acute Respiratory Distress Syndrome", The NE Journal Of Medicine, 372;8, Feb. 19, 2015, 9 pages.
Georgopoulos, Dimitris et al., "Driving Pressure during assisted mechanical ventilation—Is it controlled by patient brain?", Resp Phys & Neur228 (2016); 69-75.
Grieco, Domenico et al., "Should we use driving pressure to set tidal volume?", Current Opinion, Review, www.co-criticalcare.com, vol. 23, No. 1, Feb. 2017, 7 pages.
Kacmarek, Robert M et al., "Physiology of Ventilatory Support", Chapter 43, found online at: https://clinicalgate.com/physiology-of-ventilatory-support/, published on Jan. 6, 2015, 19 pgs.
PCT International Search Report and Written Opinion in International Application PCT/US2018/058226, dated Dec. 21, 2018, 19 pages.
YouTube Video: "Accurately setting PEEP with transpulmonary pressure", Hamilton Medical, found online at: https://www.youtube.com/watch?v=GH1rtU-1hJc#action=share, 5:09, published on Mar. 2, 2015.

\* cited by examiner

SYSTEMS AND METHODS FOR VENTILATION OF PATIENTS

CROSS-REFERENCE TO RELATED APPLICATIONS

This application claims priority to U.S. Provisional Application Ser. No. 62/725,490, filed Aug. 31, 2018, and claims priority to U.S. Provisional Application Ser. No. 62/586,077, filed Nov. 14, 2017, the complete disclosures of which are hereby incorporated herein by reference in their entireties.

SUMMARY

Patients undergoing positive pressure mechanical ventilation are at risk of experiencing ventilator-induced lung injury (VILI). VILI can be caused by mechanical ventilation that applies excessive pressure or delivers excessive volume to the lungs, causing stress or strain to lung tissue. This excess stress or strain can be particularly severe in patients with fragile or underdeveloped lungs, such as very young or premature infants, or in patients with lung disease, such as acute respiratory distress syndrome (ARDS).

Lung-protective ventilation strategies have been developed to reduce the incidence of VILI or the exacerbation of existing lung injury. These strategies include reducing the tidal volume ($V_T$), reducing the applied insufflation pressure ($\Delta P$), reducing end-inspiratory (peak inspiratory) pressure, and increasing positive end-expiratory pressure (PEEP), as a few examples. These lung-protective strategies (sometimes referred to as LPV for lung protective ventilation) are intended to prevent VILI by reducing the extent of stretch applied to the lungs by the ventilator. LPV may reduce lung injury and reduce mortality for those patients at risk of lung injury on mechanical ventilation.

However, these strategies can overcompensate for the risk of VILI, and can deliver tidal volumes that are too low for some patients. The strategies are based on collected data and experiences across populations of patients, and they provide generic guidelines that are not tailored to an individual patient. They can also fail to account for the additional diaphragmatic efforts, and resulting pressure and volume, that occur with spontaneously breathing patients.

The remainder of this disclosure describes improvements in this field to deliver safe mechanical ventilation based on a unique characterization and visualization of the patient's respiratory status.

DETAILED DESCRIPTION

The present disclosure relates to mechanical ventilation, and in particular to systems and methods for providing safe ventilation to individual patients. In an embodiment, a mechanical ventilator includes a dashboard display that identifies a patient's current ventilatory status within a global or universal ventilatory mechanics map. This dashboard display is dynamically updated with the patient's condition, and shows trends in the patient's ventilation over time. The map identifies suggested safe and unsafe regions of ventilation, and the ventilator can display informational texts, trigger auditory and/or visual alarms, and transmit alarm communications in response to determining that the patient is approaching or has entered an unsafe region. The dashboard view gives caregivers a tool for characterizing and tracking a patient's ventilatory status as it changes over time, so that the mechanical ventilation delivered to the patient can be maintained within a suggested safe zone. Safe ventilation can then be delivered by the ventilator, based on the condition and physiology of an individual patient, rather than based on more generic "lung protective" guidelines. Additionally, different individual patients can be tracked across the same universal map, so that physicians and other caregivers can use the same map as a global reference and context for all of their patients.

Figure 1:
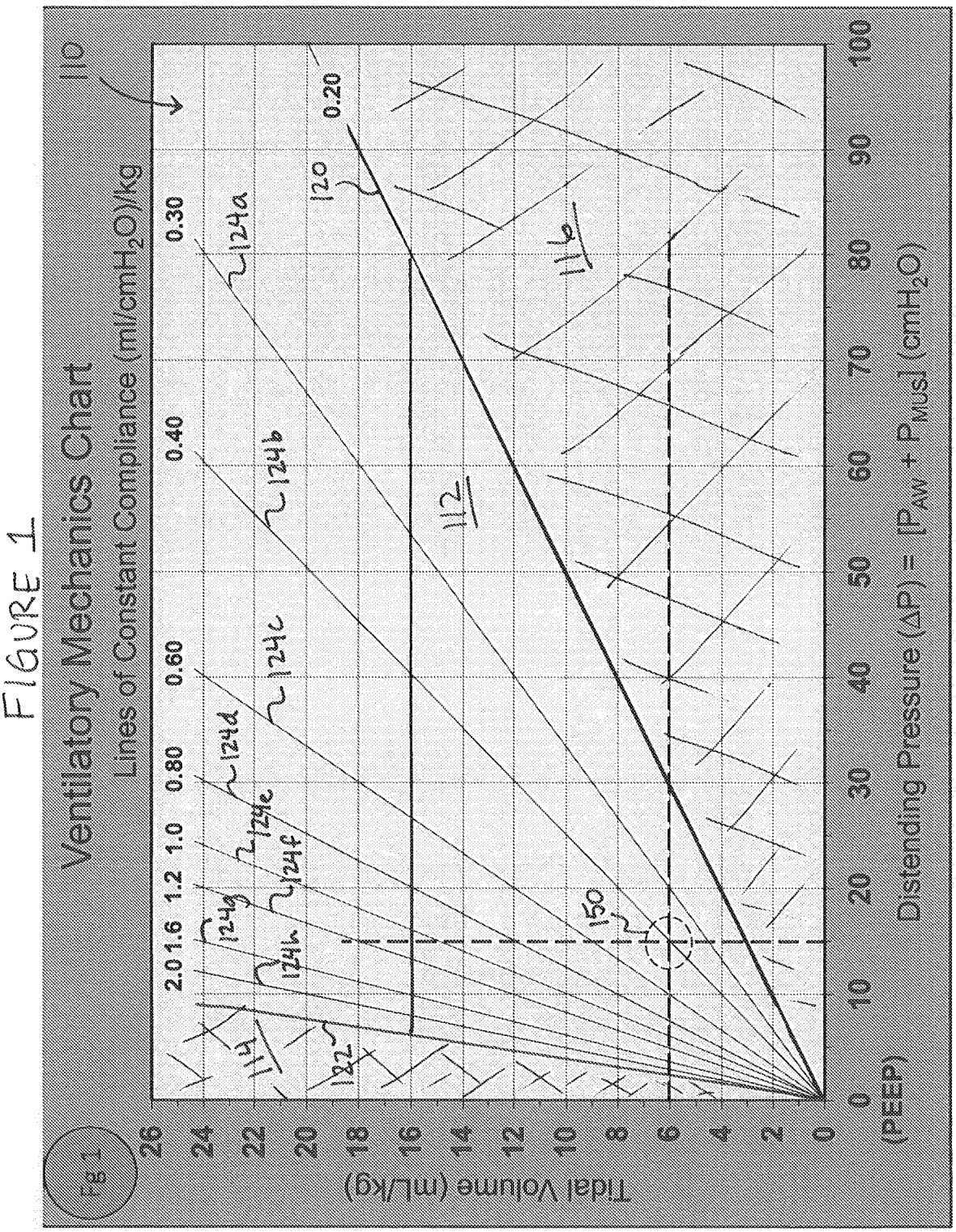
FIG. 1 illustrates a ventilatory mechanics map with a current patient status identified, according to an embodiment of the present disclosure.

An introduction to a ventilatory mechanics map 110 is shown in FIG. 1. This map 110 provides a visualization of ventilatory mechanics of human patients, normalized by their predicted body weight (as described in the next paragraph). The map 110 is defined by distending pressure (Pdist or $\Delta P$) on the x-axis, and normalized tidal volume (mL/kg) on the y-axis. Distending pressure is the total pressure applied to the lungs during an inhalation, above the PEEP level (positive end-expiratory pressure). Distending pressure is the difference in pressure between PEEP and end-inspiratory pressure. Distending pressure may also be referred to as "drive" pressure. During mechanical ventilation, the distending pressure is the sum of the pressure applied by the ventilator (Paw, or airway pressure, or also called Pvent) and the pressure applied by the patient's own diaphragmatic efforts (Pmus, or muscle pressure). That is, Pdist equals Paw plus Pmus. If a patient is spontaneously breathing, then the Pmus value will be nonzero. If the patient is not spontaneously breathing (for example, the patient is sedated), then Pmus will be zero, and Pdist equals Paw.

Normalized tidal volume is the volume of the breath (in mL), per kg of predicted body weight. Predicted body weight is an adjusted weight based on a patient's gender and height, rather than an actual weight of the patient. Predicted body weight (PBW, or sometimes referred to as ideal weight) has been found to be a good predictor of the patient's lung size. PBW can be calculated from a patient's gender and height, as height correlates proportionately with PBW. Though PBW is used in this example, the map may be created based on other indicators of lung size or ideal weight. On the y-axis of the map 110, dividing the tidal volume of a breath by PBW normalizes the tidal volume across all patient sizes, enabling patients of very different weights and lung sizes to be placed on the same map 110.

The relationship between distending pressure Pdist (on the x-axis) and resulting (normalized) tidal volume $V_T$ of the breath (on the y-axis) can be modeled as a linear relationship, as follows in Equation 1:

$$P_{dist} = V_T/C \qquad \text{Eq. 1}$$

where C is the normalized compliance of the patient's respiratory system. In this model, for a given compliance value C, increasing the distending pressure (increasing along the x-axis) will produce a tidal volume that increases linearly along an upward line, the line having a slope of 1/C. Several such lines are drawn in FIG. 1 as exemplary compliance values. These lines radiate out from the origin as spokes 120, 122, and 124a-h. Spoke 124a is associated with a compliance C of 0.30 (in mL/cmH2O/kg), spoke 124b is 0.40, 124c is 0.60, 124d is 0.80, 124e is 1.0, 124f is 1.2, 124g is 1.6, and 124h is 2.0. The boundary lines 120 and 122 represent compliance values of 0.20 and 3.33 respectively. These lines define the physiologic region 112 because compliance values below 0.20 and above 3.33 have not been documented in humans. However the chart is not limited to these specific boundary lines 120 and 122, and can be created with different boundary lines defining different regions.

Compliance is a measure of the lung's ability to stretch or expand. A low compliance value indicates that the lungs are stiff, and difficult to stretch. A high compliance value indicates that the lungs expand easily, but may not have enough resistance to recoil during exhalation. A healthy compliance value (normalized by kg) is considered to be about 1.0 (in mL/cmH2O/kg), as indicated by the line 124e.

The scales of the axes on the map 110 are chosen to span a range of breaths that are physiologically possible in human patients. For example, in FIG. 1, the x-axis ranges from zero (or a nonzero PEEP) to 100 cmH2O, and the y-axis ranges from zero to 26 mL/kg. In other embodiments, these ranges can be changed to focus on different areas of breathing or ventilation. The scales of the axes on the map 110, the spoke lines 120, 122, and 124a-h, and the boundaries of the physiologic region 112 were compiled through a thorough review of academic literature to compile pressure, volume, and compliance data from academic studies, research papers, and other publications.

The origin (the intersection of the axes) of the map 110 represents both the patient and ventilator at rest, except for the ventilator's delivery of PEEP. That is, the origin of the x-axis should be set at the value of PEEP (which could be zero or nonzero). At the origin, Pmus and Pvent are both zero, and thus tidal volume is also zero. The x-axis then shows the distending pressure above PEEP.

PEEP is the positive pressure remaining in the lungs at the end of exhalation (positive end-exhalation pressure). In mechanically ventilated patients, PEEP is typically greater than zero, so that some pressure is maintained to keep the lungs inflated and open. The distending pressure along the x-axis is intended to show the amount of pressure that was needed to deliver the resulting tidal volume (on the y-axis). This is an incremental or additional pressure above PEEP, and thus, the x-axis can be set to begin at PEEP instead of at zero. Alternatively, the x-axis can be set to begin at zero, and PEEP can be subtracted from distending pressure, giving an x-axis value of Pdist minus PEEP. In this case, Equation 1 changes to:

$$P_{dist} - PEEP = V_T/C \qquad \text{Eq. 2}$$

The map 110 of FIG. 1 can be interpreted as outlining a pressure-volume space of respiratory activity in humans. In particular, FIG. 1 includes a physiologic region 112, and non-physiologic regions 114 and 116. The physiologic region 112 is a triangular region with linear boundaries 120 and 122. As an example, for a distending pressure of 30 cmH2O (above PEEP), the physiologic region 112 begins at a normalized tidal volume of about 6 mL/kg. Below 6 mL/kg is the non-physiologic region 116. This means that in human patients, a pressure of 30 cmH2O is not expected to deliver a tidal volume less than 6 mL/kg. As another example, for a tidal volume of 5 mL/kg, the distending pressure in the physiologic region 112 ranges from about 2 to 25 cmH2O. This means that in human patients, a tidal volume of 5 mL/kg is produced by distending pressures within a range of about 2 to 25 cmH2O. On the other sides of the boundary lines 120 and 122 are the non-physiologic regions 114 and 116. These are termed "non-physiologic" because the combinations of pressure and volume are not typically found in human patients.

In an embodiment, an individual patient is plotted on the map 110 to provide a characterization of the patient's respiratory status. For example, a graphical marker such as circle 150 is placed at the location on the map 110 corresponding to the patient's most recent breath (or average of recent breaths). Specifically, FIG. 1 illustrates a single breath (or average of recent breaths) whose distending pressure was 15 cmH2O and a resulting tidal volume of 6 ml/kg. As indicated by the linear compliance spokes, the compliance indicated by this breath is about 0.40 (ml/cmH2O)/kg (along line 124b).

Figure 1A:
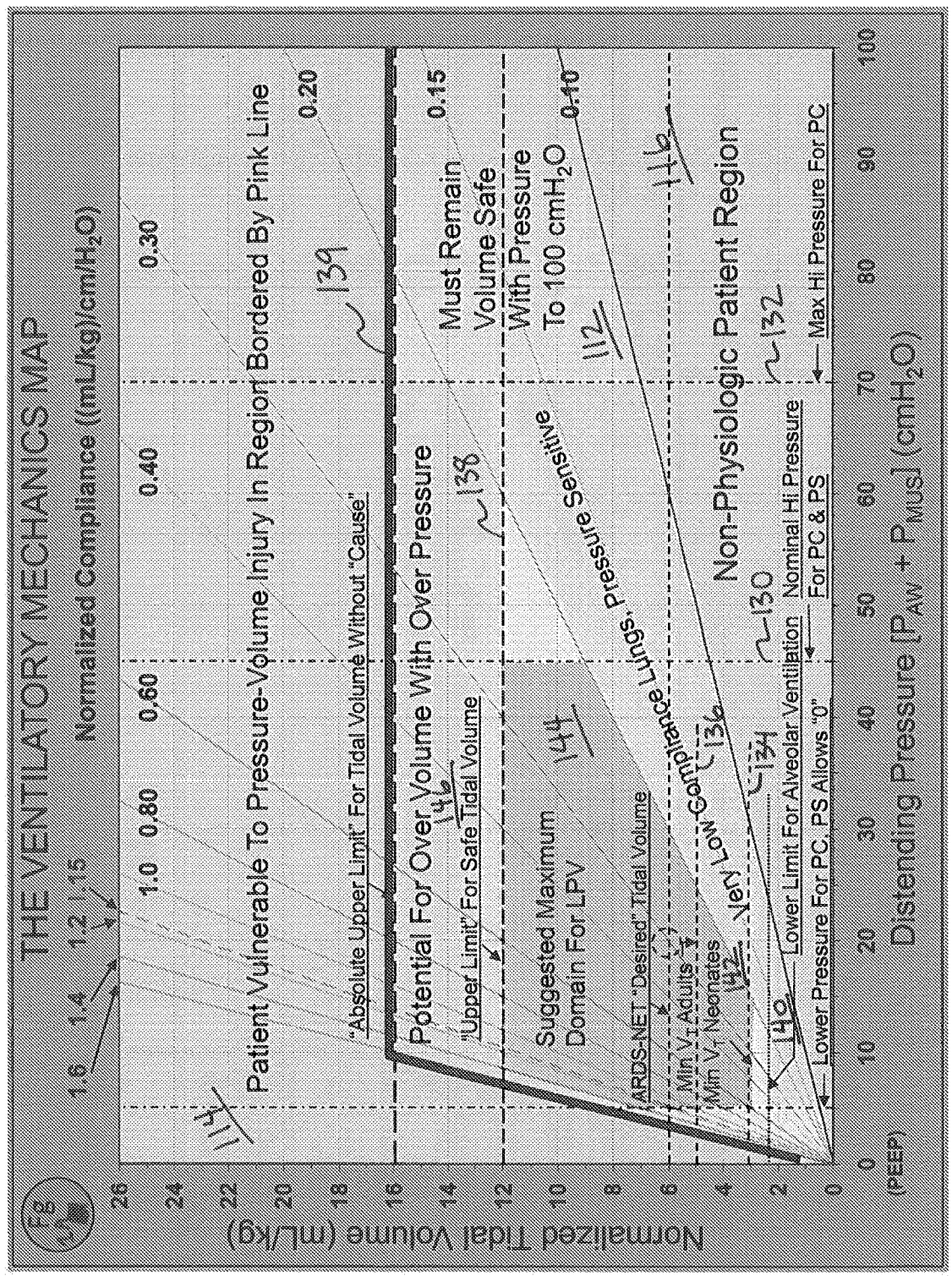
FIG. 1A illustrates a ventilatory mechanics map including suggested boundary lines and alert messages, according to an embodiment of the present disclosure.

Horizontal and vertical limits can be imposed on the map to indicate boundaries of safe ventilation. For example, turning to FIG. 1A, the map 110 is characterized by several different regions and boundaries. The map 110 includes vertical lines 130 and 132 that indicate nominal and high pressure limits, respectively, for pressure control or pressure support ventilation. Horizontal lines 134, 136, 138, and 139 indicate tidal volume limits. Line 134 indicates a threshold below which ventilation is likely inadequate; this lowest corner of the physiologic region 112 is identified as the inadequate ventilation region 140. In this region, normalized tidal volume is so low that it is likely to be insufficient to meet the patient's needs for oxygenation and gas exchange. Horizontal line 136 indicates a lower limit of suggested normalized tidal volume for mechanical ventilation of adult patients. The region 142 between lines 134 and 136 is a region of marginal ventilation for adults, and potentially acceptable ventilation for neonatal patients. In this region, normalized tidal volumes are still potentially too low, but may be acceptable in marginal cases.

The horizontal line 138 indicates an upper limit of suggested normalized tidal volume for mechanical ventilation. The region 144 bounded by compliance spoke 1.6, line 138, line 130, compliance spoke 0.20, and line 136 is the region 144 of preferred or normal ventilation. Most patients will receive adequate ventilation in this region. Finally, horizontal line 139 indicates an upper limit for normalized tidal volume, and the region 146 below that line 139 is a cautionary region of likely over-pressure or over-volume. Above line 139 are normalized tidal volumes that should not be delivered to human patients, to avoid VILI.

Figure 2:
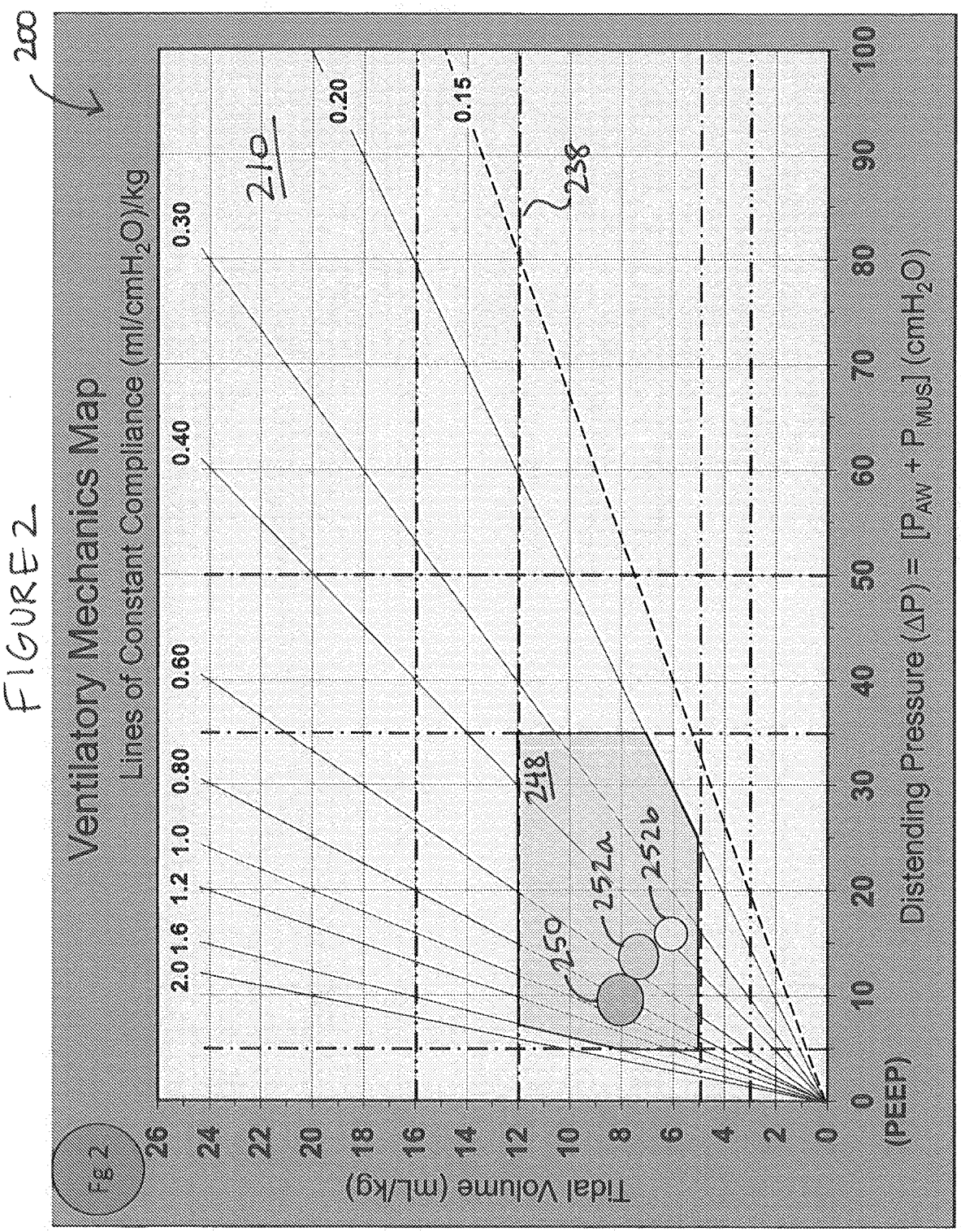
FIG. 2 illustrates a dashboard view of a ventilatory mechanics map including a patient's current status and recent trend, and suggested boundary lines, according to an embodiment of the present disclosure.

In an embodiment, the ventilatory mechanics map is presented as a dashboard view for display on a mechanical ventilator. The dashboard view shows a patient's current (or recently-averaged) respiratory status, the patient's recent trend in respiratory status, and relevant regions of target ventilation for the patient. An example is shown in FIG. 2, which shows a dashboard view 200 including a respiratory mechanics map 210. An individual patient can be placed on the map 210 based on current or recently-averaged respiratory parameters, and the patient's movement around the map can be plotted or trended over time. An embodiment of a display of patient status and trend is shown in FIG. 2. In this embodiment, a patient's current status is shown by a visual marker such as the large circle 250. The patient's previous status is identified by smaller circles 252a-b of diminishing sizes. The current status 250 can be shown in other ways than increased size, such as by using a marker or icon that has a different shape than the trend shapes 252a-b, blinks or flashes, or is displayed with a different font, outline, or color, or combinations of these options. The trend-indicating markers can also be shown in a variety of different shapes, icons, colors, lines, or similar graphic elements.

In the example shown in FIG. 2, the patient's trend shows an improving compliance C. That is, for a decreasing distending pressure (moving down from about 16 cmH2O to about 10 cmH2O from marker 252b to 250), the patient is exhibiting increasing normalized tidal volume (moving up from about 6 to about 8 mL/kg). The delivery of additional volume at the same or decreasing pressure is an indication of increasing compliance C. As compliance increases, the lungs are able to stretch further at the same pressure, resulting in a larger volume expansion.

In FIG. 2, a target region 248 has been shaded, to identify a preferred region of ventilation for this individual patient. The target region 248 is shown as an example only, and regions with different shapes or sizes can be highlighted for different patients. In FIG. 2, the region 248a is bounded by an upper compliance spoke (at normalized compliance value of 1.6), an upper tidal volume limit (at 12 mL/kg) (labeled as boundary 238), an upper pressure limit (at 35 cmH2O), a lower compliance spoke (at a value of 0.20), a lower tidal volume limit (at 5 mL/kg), and a lower pressure limit (at 5 cmH2O). This region 248 is a target area for ventilation of the current patient (the patient whose breaths are shown with markers 250, 252a, 252b). Region 248 was identified based the patient's physiologic condition and/or disease state, and associated upper and lower limits for tidal volume, distending pressure, and compliance, in order to ventilate the patient within these parameters. These boundaries may differ for other patients, based on their physiology, disease state, or other factors.

In an embodiment, a mechanical ventilator triggers an alert or alarm based on a determination that the patient is approaching or has crossed a boundary on a dashboard 200 or a map 110, 210. For example, in the example shown in FIG. 2, the normalized tidal volume being delivered to the patient is increasing, moving the patient's location 250 on the map upward toward the boundary 238. The ventilator can trigger an alert or alarm if the patient's location 250 reaches or crosses the boundary line 238, or when the patient's location 250 moves within a proximity (such as a buffer distance) of the line 238. As an example, referring to FIG. 2, the ventilator is programmed to sound an alarm when the patient's location 250 moves within 0.5 mL/kg (a buffer distance) of the line 238. As an example, the marker 250 can have a first color to indicate that compliance is increasing (such as a green color) or a second color to indicate that compliance is decreasing (such as a red color). The marker could also include an up or down arrow to show recent trend at a glance. These visual cues can help display the patient's state or trend even before reaching a boundary or buffer.

In an embodiment, the boundary lines that determine the safe areas of ventilation, or that are used for alarms or alerts, can be adjusted by a user. For example, any of the boundary lines (such as lines 130, 132, 134, 136, 138, and 139 in FIG. 1A, or any compliance spoke boundaries) can be moved, adjusted, or removed by a user based on a patient's current condition, procedure, or treatment. The ventilator then adjusts its alerts or alarms accordingly, so that the alerts or alarms are triggered at the positions on the map desired by the user. An alert or alarm may be any combination of audible, visual, graphic, textual, kinetic, or other messages that inform a clinician to attend to the ventilator and the patient.

In an embodiment, a ventilator is programmed to adjust a setting in response to such an alert or alarm. For example, the ventilator can adjust a setting by one increment (moving a pressure or volume target down by an incremental amount, for example), while continuing to operate the alert or alarm. This empowers the ventilator to take an automatic step to address the potentially unsafe condition, without providing complete closed-loop control to the ventilator. In an embodiment, a ventilator reduces a calculated pressure target by a set amount (such as 5, 10, 15, or 20 cmH2O or other values) in response to an alarm triggered by the dashboard 200 or map 110, 210.

In another embodiment, the map 110, 210 is used in connection with a closed-loop ventilator system in which the ventilator adjusts settings automatically based on the patient's ventilatory status, and displays the patient's current, recently-averaged, and/or trending respiratory status on a dashboard display 200 such as on the map 210, 110. A ventilator that is operated by a closed-loop control system can visually locate the patient on the map 110, 210, enabling the clinician to visualize the patient's ventilatory status and confirm the proper operation of the closed-loop controller to maintain the patient in a safe zone. The processor that executes the program instructions for identifying the patient status and displaying it on the map 110, 210 can be integrated as part of a closed-loop controller, or can be housed in a different system, such as part of the ventilator, the ventilator display, or a separate processor and display.

The dashboard 200 featuring the respiratory mechanics map 210, 110 is a useful tool for a medical caregiver attending to a patient on a mechanical ventilator, and is advantageous in that the same map 210, 110 can be used for all patients, regardless of gender, age, size, or medical condition. As a result, caregivers can become familiar with one map of respiratory mechanics and can quickly identify when an individual patient is moving into an unsafe or problematic region on the map. The map provides the caregiver with a single reference frame in which to evaluate most or all individual patients.

Figure 3:
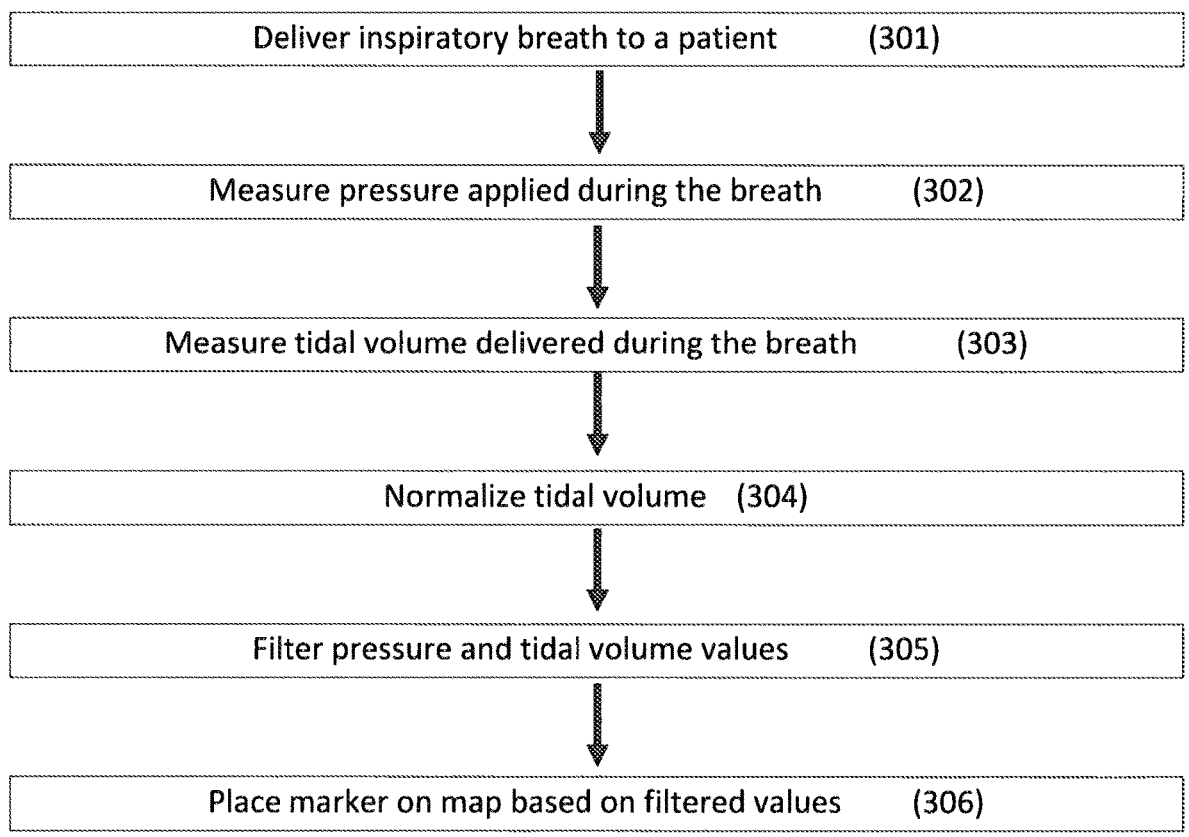
FIG. 3 is a flowchart depicting a method of utilizing a respiratory mechanics map to deliver ventilation to a patient, according to an embodiment of the present disclosure.

FIG. 3 is a flowchart depicting a method of utilizing a respiratory mechanics map to deliver ventilation to a patient. According to an embodiment, the method includes delivering an inspiratory breath to a patient, at 301. The method includes measuring the pressure applied by the mechanical ventilator during the breath, at 302. The measured pressure can be an end-inspiratory pressure measured by the ventilator at the end of the breath, or a pressure target calculated by the ventilator for the breath. The method also includes measuring the total tidal volume delivered by the ventilator to the patient during the breath, at 303. The method then includes normalizing the tidal volume, such as by dividing by PBW, at 304. The method includes filtering the pressure and tidal volume values, at 305. This step could encompass discarding measurements that are outliers, that appear to be non-physiological, that were disturbed (such as by the patient coughing), or fail quality or noise checks. The filter could also or alternatively include adding the measured values to a running average, based on equal or non-equal weights (such as weighting new values more or less than the prior average). Many other methods for filtering measurements taken by a medical ventilator may be applied here. Finally, at 306, the method includes placing a marker (such as circle 150) on the map 110 at the position corresponding to the filtered pressure and volume values.

The method of FIG. 3 contemplates plotting a patient's position based on pressure and volume. With those values and the map 110, 210, the patient's compliance C can be determined, by identifying the slope (or spoke 124) that crosses that position on the map. Knowledge of the patient's compliance C can be useful in assessing the patient's condition, as described above. The method of FIG. 3 is particularly useful in sedated patients, where Pmus is zero (because the patient is not initiating or contributing to breaths), and thus distending pressure equals Pvent, which can be measured directly. When the patient is plotted on the map 110, 210, the patient's normalized compliance value C can be determined. This can be useful for particular types of patients (such as patients with ARDS), in order to evaluate improving or declining compliance.

However, with spontaneously breathing patients, distending pressure Pdist (along the x-axis) can be difficult to measure, due to the contribution of Pmus by the patient. Pmus is the pressure applied by the patient's diaphragmatic effort, and this pressure can be difficult to measure. Existing methods for measuring Pmus include invasive use of balloon catheters, or manipulation of a delivered breath to add a pause at the end of inspiration.

Notably, the dashboard 200 with map 110, 210 enables Pdist to be determined in actively breathing patients, even with Pmus is unknown. This can be done by measuring the tidal volume and obtaining a measurement or estimate of the patient's compliance C. The patient's compliance C can be measured by applying an end-inspiratory hold during a proportional assist mode of ventilation, such as PAV+ ventilation from Medtronic (Boulder, Colo.). Proportional assist ventilation is particularly well-suited for compliance measurements, as the flow of gas delivered by the ventilator during inspiration is driven by the patient's demand, and the ventilator ceases delivery of flow then the patient voluntarily ends the breath. The ventilator is synchronized with the patient, and amplifies the patient's efforts to breathe. As a result, the ventilator ends its delivery of gas when the patient ends his or her diaphragmatic activity, and at that moment at the end of inspiration, Pmus is zero. During a very brief end-inspiratory hold while Pmus is zero, the ventilator measures the end-inspiratory pressure. With that pressure measurement, and the tidal volume of that same breath, the ventilator can calculate the patient's compliance C according to Equations 1 or 2 above. For more information on this method, see U.S. Provisional Application No. 62/586,077, the contents of which area incorporated herein by reference.

Figure 4:
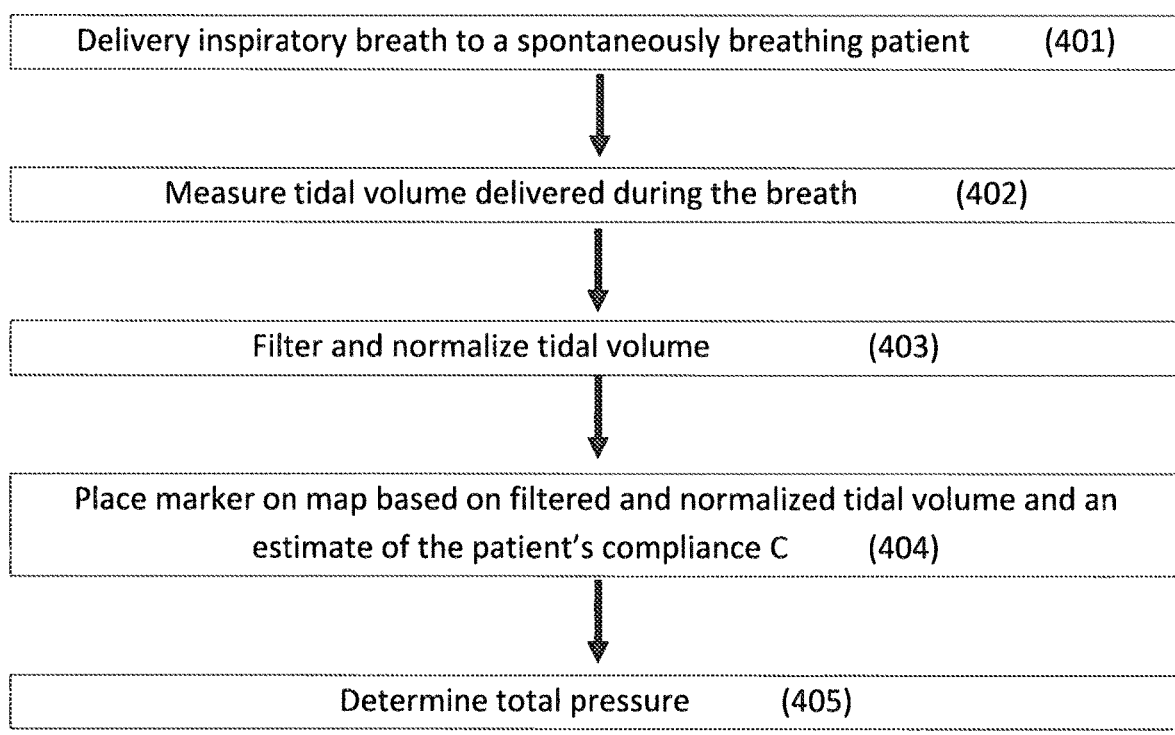
FIG. 4 is a flowchart depicting a method of utilizing a respiratory mechanics map to deliver ventilation to a spontaneously breathing patient, according to an embodiment of the present disclosure.

With a measurement or estimate of the patient's compliance C, the patient can be located on the map 110, 210 following the method of FIG. 4, in an embodiment. According to this embodiment, a method includes delivering an inspiratory breath to a spontaneously breathing patient, at 401. The method includes measuring the tidal volume delivered during the breath at 402, and filtering and normalizing the tidal volume at 403. At 404, the method includes placing a marker (such as marker 250) on the map 110, 210 based on the tidal volume and a measurement or estimate of the patient's compliance C. Finally, the method includes determining total distending pressure Pdist, at 405. Total distending pressure can be determined from the x-axis value that corresponds to the position of the marker on the map. Thus, the total distending pressure can be determined even when the patient's contribution Pmus is unknown or not measured directly. Determining distending pressure is very valuable in actively breathing patients, where otherwise measuring Pvent without knowing the contribution of Pmus may result in an under-estimation of Pdist. The method of FIG. 4 enables lung-protective strategies to be employed in spontaneously breathing patients based on distending pressure, taking into account both Pvent and Pmus, rather than addressing lung protective strategies through other values such as tidal volume.

Figure 5:
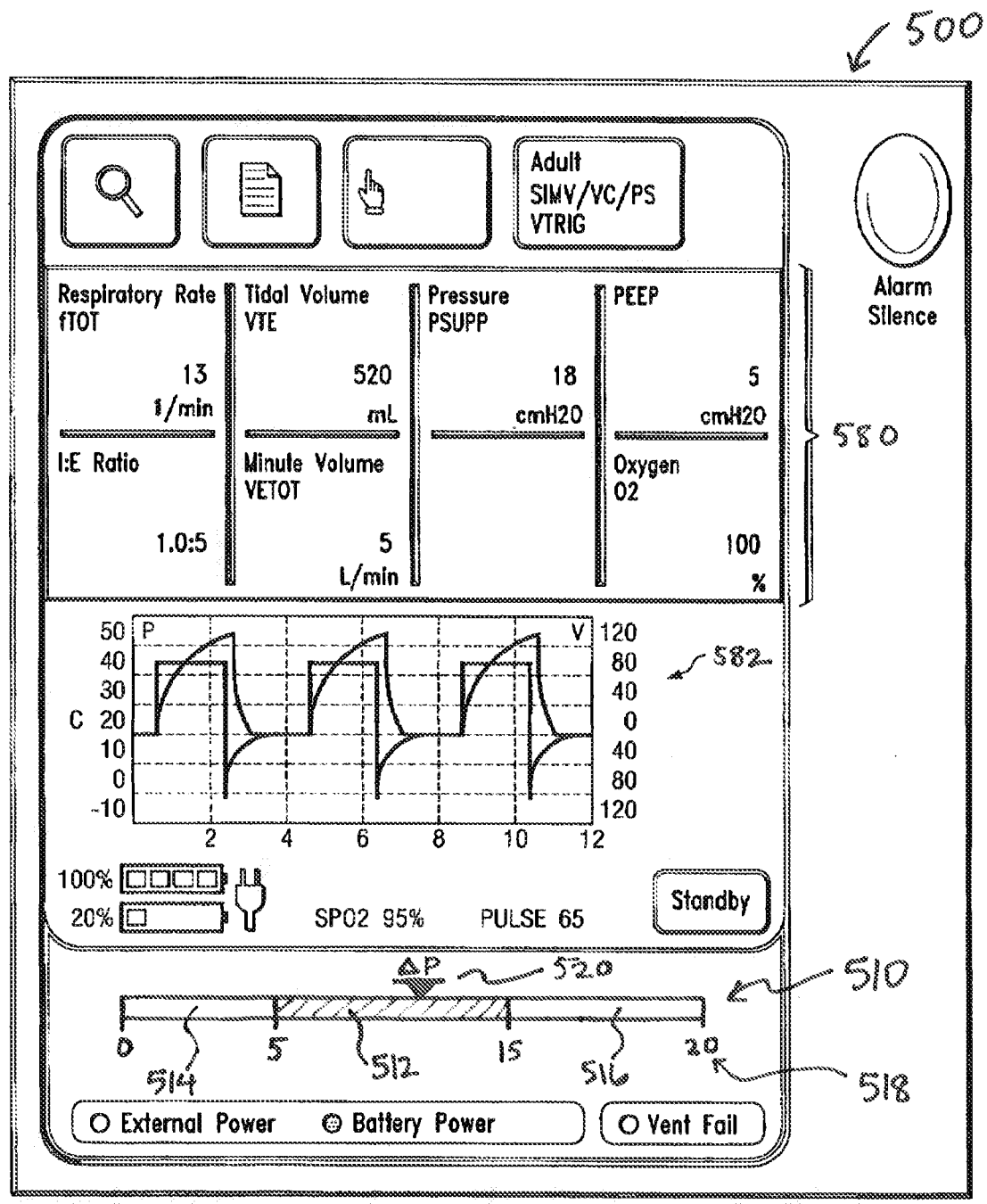
FIG. 5 illustrates a view of a distending pressure bar, according to an embodiment of the present disclosure.

In an embodiment, total distending pressure Pdist is plotted in bar format as shown in FIG. 5. In the embodiment of FIG. 5, a display screen 500 includes a parameter display 580, a waveform graphical display 582, and a distending pressure bar 510. The bar 510 includes pressure values along a scale, such as values from 0 at the left end of the bar to 40, 50, 60, or 70 at the right end (in cmH2O). Different ranges of pressure values are highlighted along the bar to indicate safe and unsafe pressure for the patient's lungs. For example, as shown in FIG. 5, a safe range 512 is indicated by brackets, shading, hatching, color, or other graphics, between values of 5 and 15 cmH2O. To the left of the safe range 512 is an unsafe range 514 of underpressure (between 0 and 5 cmH2O), and to the right of the safe range is an unsafe range of 516 (between 15 and 20 cmH2O), followed to the right by an over-pressure limit 518 (set at 20 cmH2O). The patient's current distending pressure, as determined from the map 110, 210 (for example, by the method of FIG. 3 or 4) is indicated by the marker 520. In FIG. 5, the marker 520 is positioned in the safe zone 512, indicating that the total distending pressure that is being applied to the patient's lungs is within a safe range. The ventilator can be programmed to trigger alarms based on a determination that the marker 520 is approaching or has crossed a boundary into an unsafe range.

Figure 6:
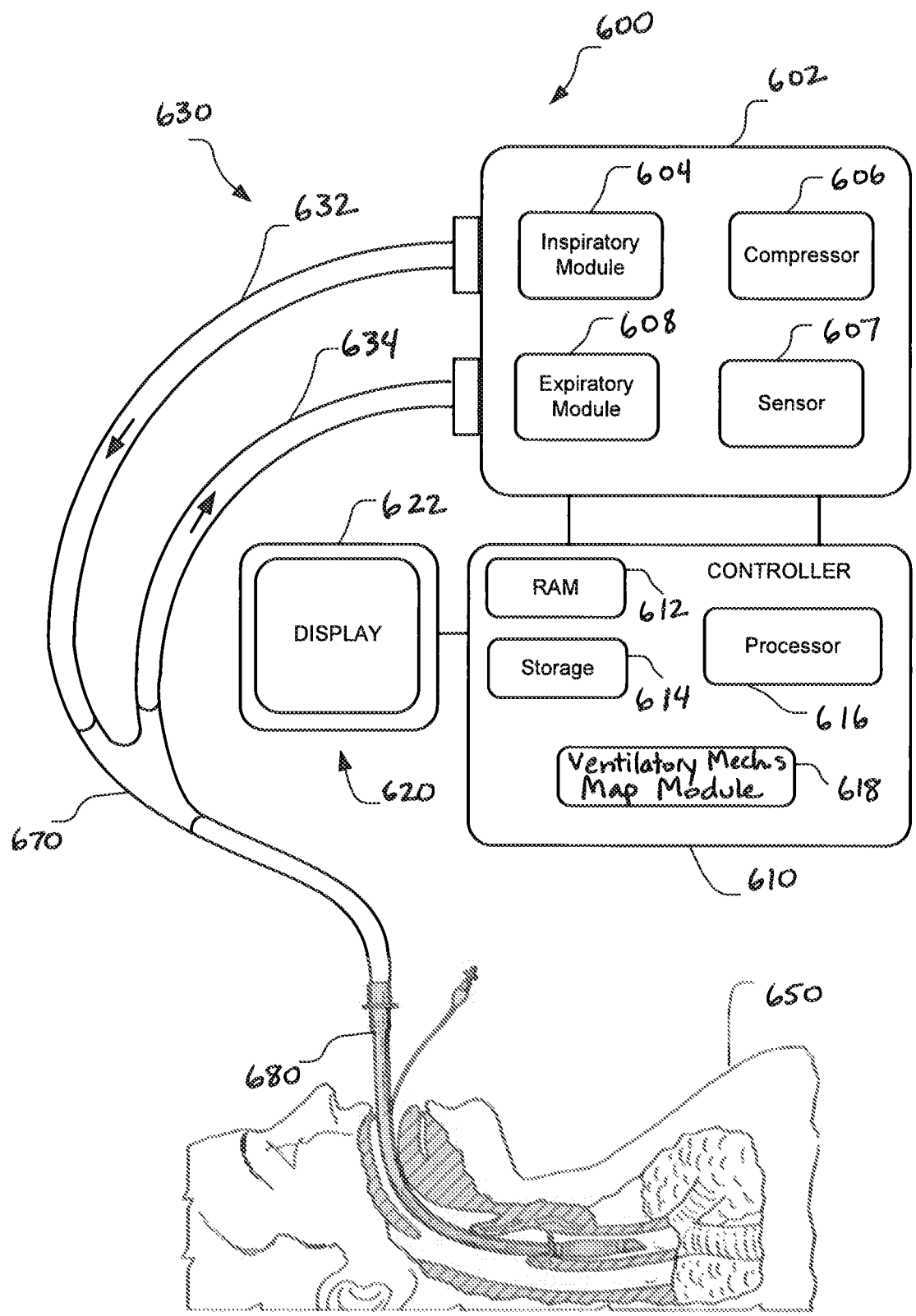
FIG. 6 is schematic diagram illustrating a ventilator ventilating a patient utilizing a respiratory mechanics dashboard, according to an embodiment of the present disclosure.

FIG. 6 is a diagram illustrating an aspect of an exemplary ventilator 600 connected to a human patient 650. Ventilator 600 includes a pneumatic system 602 (also referred to as a pressure generating system 602) for circulating breathing gases to and from patient 650 via the ventilation tubing system 630, which couples the patient 650 to the pneumatic system 602 via an invasive (e.g., endotracheal tube, as shown) or a non-invasive (e.g., nasal mask) patient interface 680.

Ventilation tubing system 630 (or patient circuit 630) may be a two-limb (shown) or a one-limb circuit for carrying gases to and from the patient 650. In a two-limb aspect, a fitting, typically referred to as a "wye-fitting" 670, may be provided to couple a patient interface 680 (as shown, an endotracheal tube) to an inspiratory limb 632 and an expiratory limb 634 of the ventilation tubing system 630.

Pneumatic system 602 may be configured in a variety of ways. In the present example, pneumatic system 602 includes an expiratory module 608 coupled with the expiratory limb 134 and an inspiratory module 604 coupled with the inspiratory limb 632. Compressor 606 or other source(s) of pressurized gases (e.g., air, oxygen, and/or helium) is coupled with inspiratory module 604 and the expiratory module 608 to provide a gas source for ventilatory support via inspiratory limb 632.

The inspiratory module 604 is configured to deliver gases to the patient 650 according to prescribed ventilatory settings. In some aspects, inspiratory module 604 is configured to provide ventilation according to various breath types, e.g., via volume-control, pressure-control, or via any other suitable breath types.

The expiratory module 608 is configured to release gases from the patient's lungs according to prescribed ventilatory settings. Specifically, expiratory module 608 is associated with and/or controls an expiratory valve for releasing gases from the patient 650.

The ventilator 600 may also include one or more sensors 607 communicatively coupled to ventilator 600. The sensors 607 may be located in the pneumatic system 602, ventilation tubing system 630, and/or on the patient 650. The aspect of FIG. 6 illustrates a sensor 607 in pneumatic system 602.

Sensors 607 may communicate with various components of ventilator 600, e.g., pneumatic system 602, other sensors 607, processor 616, ventilatory mechanics map module 618, and any other suitable components and/or modules. A module as used herein refers to memory, one or more processors, storage, and/or other components of the type commonly found in command and control computing devices.

In one aspect, sensors 607 generate output and send this output to pneumatic system 602, other sensors 607, processor 616, ventilatory mechanics map module 618, and any other suitable components and/or modules. Sensors 607 may employ any suitable sensory or derivative technique for monitoring one or more patient parameters or ventilator parameters associated with the ventilation of a patient 650. Sensors 607 may detect changes in patient parameters indicative of patient triggering, for example. Sensors 607 may be placed in any suitable location, e.g., within the ventilatory circuitry or other devices communicatively coupled to the ventilator 600. Further, sensors 607 may be placed in any suitable internal location, such as, within the ventilatory circuitry or within components or modules of ventilator 600. For example, sensors 607 may be coupled to the inspiratory and/or expiratory modules for detecting changes in, for example, circuit pressure and/or flow. In other examples, sensors 607 may be affixed to the ventilatory tubing or may be embedded in the tubing itself. According to some aspects, sensors 607 may be provided at or near the lungs (or diaphragm) for detecting a pressure in the lungs. Additionally or alternatively, sensors 607 may be affixed or embedded in or near wye-fitting 670 and/or patient interface 680. Indeed, any sensory device useful for monitoring changes in measurable parameters during ventilatory treatment may be employed in accordance with aspects described herein.

The pneumatic system 602 may include a variety of other components, including mixing modules, valves, tubing, accumulators, filters, etc. Controller 610 is operatively coupled with pneumatic system 602, signal measurement and acquisition systems, and an operator interface 620 that may enable an operator to interact with the ventilator 600 (e.g., change ventilator settings, select operational modes, view monitored parameters, etc.).

In one aspect, the operator interface 620 of the ventilator 600 includes a display 622 communicatively coupled to ventilator 600. Display 622 provides various input screens, for receiving clinician input, and various display screens, for presenting useful information to the clinician. In one aspect, the display 622 is configured to include a graphical user interface (GUI). The GUI may be an interactive display, e.g., a touch-sensitive screen or otherwise, and may provide various windows and elements for receiving input and interface command operations. Alternatively, other suitable means of communication with the ventilator 600 may be provided, for instance by a wheel, keyboard, mouse, or other suitable interactive device. Thus, operator interface 620 may accept commands and input through display 622. Display 622 may also provide useful information in the form of various ventilatory data regarding the physical condition of a patient 650. The useful information may be derived by the ventilator 600, based on data collected by a processor 616, and the useful information may be displayed to the clinician in the form of graphs, wave representations, pie graphs, text, or other suitable forms of graphic display. For example, patient data may be displayed on the GUI and/or display 622. Additionally or alternatively, patient data may be communicated to a remote monitoring system coupled via any suitable means to the ventilator 600. In one aspect, the display 622 may display one or more of a current patient effort, a percent support setting, a reduced percent support setting, an increased percent support setting, a notification of a reduced percent support setting, and a notification of a return to a set or desired percent support setting.

Controller 610 may include memory 612, one or more processors 616, storage 614, and/or other components of the type commonly found in command and control computing devices. Controller 610 may further include an ventilatory mechanics map module 618 configured to deliver gases to the patient 650 according to prescribed breath types as illustrated in FIG. 6. In alternative aspects, the ventilatory mechanics map module 618 may be located in other components of the ventilator 600, such as the pressure generating system 602 (also known as the pneumatic system 602).

The memory 612 includes non-transitory, computer-readable storage media that stores and/or encodes software (such as computer executable instruction) that is executed by the processor 616 and which controls the operation of the ventilator 600. In an aspect, the memory 612 includes one or more solid-state storage devices such as flash memory chips. In an alternative aspect, the memory 612 may be mass storage connected to the processor 616 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 616. That is, computer-readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

In an embodiment, the controller includes a respiratory mechanics map module 618 that generates a respiratory mechanics map and/or dashboard view as described in detail throughout the above.

The systems and methods described here may be provided in the form of tangible and non-transitory machine-readable medium or media (such as a hard disk drive, hardware memory, etc.) having instructions recorded thereon for execution by a processor or computer. The set of instructions may include various commands that instruct the computer or processor to perform specific operations such as the methods and processes of the various embodiments described here. The set of instructions may be in the form of a software program or application. The computer storage media may include volatile and non-volatile media, and removable and non-removable media, for storage of information such as computer-readable instructions, data structures, program modules or other data. The computer storage media may include, but are not limited to, RAM, ROM, EPROM, EEPROM, flash memory or other solid state memory technology, CD-ROM, DVD, or other optical storage, magnetic disk storage, or any other hardware medium which may be used to store desired information and that may be accessed by components of the system. Components of the system may communicate with each other via wired or wireless communication. The components may be separate from each other, or various combinations of components may be integrated together into a medical monitor or processor, or contained within a workstation with standard computer hardware (for example, processors, circuitry, logic circuits, memory, and the like). The system may include processing devices such as microprocessors, microcontrollers, integrated circuits, control units, storage media, and other hardware.

Although exemplary embodiments have been described and illustrated, it should be understood that changes and modifications to these exemplary embodiments are also within the intended scope of this disclosure.

What is claimed is:

1. A method for operating a positive pressure mechanical ventilator, comprising:
   delivering, with a mechanical ventilator, an inspiration breath to a patient;
   displaying, on a display screen of the mechanical ventilator, a dashboard comprising a ventilatory mechanics map relating tidal volume versus distending pressure;
   plotting on the map a marker at a first location representing a first tidal volume measurement and a first distending pressure measurement from the inspiration breath or recently averaged breaths;
   moving the marker on the map to a second location representing a second tidal volume measurement and a second distending pressure measurement from at least one subsequent breath delivered to the patient; and
   displaying on the map a history of recent locations of the marker.

2. The method of claim 1, wherein the map outlines a pressure-volume space of respiratory activity for the patient.

3. The method of claim 1, wherein the map includes boundary lines identifying a region of safe ventilation for the patient, wherein the boundary lines include at least one boundary line for the tidal volume and at least one boundary line for the distending pressure.

4. The method of claim 3, further comprising:
   triggering an alert or alarm when the marker has coordinates outside of the region of safe ventilation.

5. The method of claim 3, wherein the boundary lines are adjustable by a user.

6. The method of claim 3, wherein the map further includes a region of preferred ventilation inside of the region of safe ventilation for the patient.

7. The method of claim 3, wherein the boundary lines include:
   at least one vertical line; and
   at least one horizontal line.

8. The method of claim 7, wherein the at least one vertical line represents a boundary for the distending pressure on the map.

9. The method of claim 7, wherein the boundary lines further include at least one diagonal line based on a lung compliance.

10. The method of claim 3, wherein the boundary lines on the map include:
    at least one vertical line;
    two horizontal lines; and
    at least one diagonal line.

11. The method of claim 1, wherein the history of recent locations of the marker are indicative of at least one trend of respiratory activity for the patient.

12. The method of claim 1, wherein the map visually identifies a preferred region of ventilation for the patient.

13. The method of claim 12, wherein the preferred region of ventilation is determined based on one or more of:
    a physiologic condition of the patient,
    a disease state of the patient,
    an upper tidal volume limit for the patient,
    a lower tidal volume limit for the patient,
    an upper distending pressure limit for the patient,
    a lower distending pressure limit for the patient, or
    a compliance for the patient.

14. The method of claim 1, wherein the marker has a circular shape.

15. The method of claim 1, wherein the marker at the second location includes a current status indicator, the current status indicator including at least one of:
    an increase in size from the marker at the first location;
    a different shape than the marker at the first location;
    a blinking effect; or
    a different color than the marker at the first location.

16. The method of claim 1, wherein the history of recent locations of the marker includes a historical marker at the first location having a diminished size relative to the marker at the second location.

17. A positive pressure mechanical ventilator, comprising:
    a pneumatic system;
    a display screen; and
    a controller comprising at least one processor and at least one memory storing computer-executable instructions that when executed by the at least one processor cause the mechanical ventilator to:
    deliver an inspiration breath to a patient;
    display, on the display screen, a dashboard comprising a ventilatory mechanics map relating tidal volume versus distending pressure;
    plot on the map a first marker at a first location representing a first tidal volume measurement and a first distending pressure measurement from the inspiration breath or recently averaged breaths;
    plot on the map a second marker at a second location representing a second tidal volume measurement and a second distending pressure measurement from at least one subsequent breath delivered to the patient; and
    display on the map a history of recent locations of the marker as indicated at least by a relative size of the first marker and the second marker.

18. The mechanical ventilator of claim 17, wherein the map identifies boundaries of safe ventilation for the patient.

19. The mechanical ventilator of claim 18, the computer-executable instructions further causing the mechanical ventilator to:
    trigger an alert or alarm when patient data crosses a boundary of safe ventilation.

20. A graphical user interface communicatively coupled to a controller of a positive pressure mechanical ventilator, the controller causing the graphical user interface to provide a dashboard, comprising:
- providing a ventilatory mechanics map relating tidal volume versus distending pressure;
- receiving a first tidal volume measurement and a first distending pressure measurement for at least one inspiration breath delivered to a patient by the mechanical ventilator;
- placing on the map a marker at a first location representing the first tidal volume measurement and the first distending pressure measurement;
- receiving a second tidal volume measurement and a second distending pressure measurement for at least one subsequent breath delivered to the patient by the mechanical ventilator; and
- moving the marker on the map to a second location representing the second tidal volume measurement and the second distending pressure measurement.

* * * * *